United States Patent
Miyajima

(10) Patent No.: US 10,685,547 B2
(45) Date of Patent: *Jun. 16, 2020

(54) COMMUNICATION DEVICE, INFORMATION PROCESSING SYSTEM, RECORDING MEDIUM, AND INFORMATION PROCESSING METHOD

(71) Applicant: SONY CORPORATION, Tokyo (JP)

(72) Inventor: Yasushi Miyajima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/515,388

(22) Filed: Jul. 18, 2019

(65) Prior Publication Data

US 2019/0340910 A1    Nov. 7, 2019

Related U.S. Application Data

(63) Continuation of application No. 15/743,164, filed as application No. PCT/JP2016/063467 on Apr. 28, 2016, now Pat. No. 10,403,112.

(30) Foreign Application Priority Data

Jul. 28, 2015    (JP) ................................. 2015-148704

(51) Int. Cl.
*G08B 23/00*    (2006.01)
*G08B 21/02*    (2006.01)
(Continued)

(52) U.S. Cl.
CPC ............ *G08B 21/02* (2013.01); *A61B 5/0022* (2013.01); *A61B 5/411* (2013.01); *G06Q 30/02* (2013.01); *H04M 1/7253* (2013.01); *H04M 11/00* (2013.01); *H04W 4/06* (2013.01); *A61B 5/01* (2013.01); *A61B 5/021* (2013.01); *A61B 5/024* (2013.01); *A61B 5/0476* (2013.01);
(Continued)

(58) Field of Classification Search
CPC ..... G08B 21/02; H04M 1/7253; H04M 11/00; G06Q 30/02; A61B 5/0022; A61B 5/411; A61B 5/024; A61B 5/021; A61B 5/0476; A61B 5/7264; A61B 5/1118; A61B 5/01; A61B 5/746; H04W 4/06
USPC ...................................................... 340/573.1
See application file for complete search history.

(56) References Cited

U.S. PATENT DOCUMENTS

2006/0200480 A1    9/2006 Harris et al.

FOREIGN PATENT DOCUMENTS

AU    2006218537 A1    9/2006
BR    PI0608266 A2    11/2010
(Continued)

OTHER PUBLICATIONS

International Search Report and Written Opinion of PCT Application No. PCT/JP2016/063467, dated Jul. 19, 2016, 10 pages of English Translation and 08 pages of ISRWO.
(Continued)

*Primary Examiner* — Tanmay K Shah
(74) *Attorney, Agent, or Firm* — Chip Law Group

(57) ABSTRACT

Provided is a communication device including a control unit that acquires current situation information of a first user based on an attribute of the first user and a current situation of the first user, and a communication unit that, in accordance with control by the control unit, transmits the current situation information of the first user to a surrounding communication device.

16 Claims, 18 Drawing Sheets

(51) Int. Cl.

| | | |
|---|---|---|
| *A61B 5/00* | (2006.01) | |
| *G06Q 30/02* | (2012.01) | |
| *H04M 1/725* | (2006.01) | |
| *H04M 11/00* | (2006.01) | |
| *H04W 4/06* | (2009.01) | |
| *A61B 5/01* | (2006.01) | |
| *A61B 5/021* | (2006.01) | |
| *A61B 5/024* | (2006.01) | |
| *A61B 5/0476* | (2006.01) | |
| *A61B 5/11* | (2006.01) | |

(52) U.S. Cl.
CPC .......... *A61B 5/1118* (2013.01); *A61B 5/7264* (2013.01); *A61B 5/746* (2013.01)

(56) References Cited

FOREIGN PATENT DOCUMENTS

| | | |
|---|---|---|
| CA | 2599692 A1 | 9/2006 |
| CN | 101529409 A | 9/2009 |
| EP | 1875369 A2 | 1/2008 |
| JP | 2001-338067 A | 12/2001 |
| JP | 2003-109160 A | 4/2003 |
| JP | 2005-173854 A | 6/2005 |
| JP | 2007-025853 A | 2/2007 |
| JP | 2008-537614 A | 9/2008 |
| JP | 2009-157485 A | 7/2009 |
| JP | 2009-157551 | 7/2009 |
| JP | 2009-157551 A | 7/2009 |
| JP | 4997617 A | 8/2012 |
| JP | 4997617 B1 | 8/2012 |
| JP | 2013-070142 A | 4/2013 |
| JP | 2014-123214 A | 7/2014 |
| JP | 2015-108854 A | 6/2015 |
| KR | 10-2007-0116037 A | 12/2007 |
| MX | 2007010726 A | 11/2008 |
| WO | 2006/094086 A2 | 9/2006 |
| WO | 2013/061856 A1 | 5/2013 |
| WO | 2013/121737 A1 | 8/2013 |
| WO | 2014/097671 A1 | 6/2014 |

OTHER PUBLICATIONS

Non-Final Office Action for U.S. Appl. No. 15/743,164 dated Nov. 28, 2018, 17 pages.
Notice of Allowance for U.S. Appl. No. 15/743,164 dated Apr. 17, 2019, 05 pages.
International Preliminary Report on Patentability of PCT Application No. PCT/JP2016/063467, dated Feb. 8, 2018, 10 pages of English Translation and 05 pages of IPRP.
Office Action for JP Patent Application No. 2017-531039, dated Nov. 26, 2019, 6 pages of Office Action and 5 pages of English Translation.
Office Action for JP Patent Application No. 2017-531039, dated Feb. 4, 2020, 05 pages of Office Action and 04 pages of English Translation.

COMMUNICATION DEVICE, INFORMATION PROCESSING SYSTEM, RECORDING MEDIUM, AND INFORMATION PROCESSING METHOD

CROSS REFERENCE TO RELATED APPLICATIONS

The present application is a continuation application of U.S. patent application Ser. No. 15/743,164, filed on Jan. 9, 2018, which is a National Stage Entry of Patent Application No. PCT/JP2016/063467 filed on Apr. 28, 2016, which claims priority from prior Japanese Patent Application JP 2015-148704 filed in the Japan Patent Office on Jul. 28, 2015, the entire contents of which are hereby incorporated by reference.

TECHNICAL FIELD

The present disclosure relates to a communication device, an information processing system, a recording medium, and an information processing method.

BACKGROUND ART

Today, information processing and communication technology are maturing, and information processing systems that appropriately match people needing help in social life with people having the ability to help are being proposed.

For example, Patent Literature 1 proposes a service that stores and matches information about care recipients and caregivers with each other. Also, Patent Literature 2 proposes selecting an optimal provider corresponding to information about a user needing nursing care during an emergency and current position information about the user, and issuing notifications to the terminals of both the provider and the user.

CITATION LIST

Patent Literature

Patent Literature 1:
JP 2001-338067A
Patent Literature 2:
JP 2005-173854A

DISCLOSURE OF INVENTION

Technical Problem

However, even if someone is having trouble nearby, such as on a train, in a shop, on the street, or at a friend's home, a person who wants to perform a small act of kindness will be unable to help unless that person notices and understands the situation correctly. For example, even if a person wants to give up one's own seat on a train to someone who is pregnant or injured, that person may be unable to tell whether or not someone is pregnant on sight. Even if one of the recently popular maternity marks is affixed to a bag or the like, there are problems such as the mark being in a blind spot, or not noticing the mark unless one comes closer. Also, even if a person wants someone else to give up their seat, it is difficult for the person to ask for the seat directly.

Meanwhile, methods utilizing a social networking service (SNS) or the like as a means of sharing information widely are conceivable, but such methods are unsuited to notifying bystanders in the immediate vicinity that oneself is having trouble.

Accordingly, the present disclosure proposes a communication device, an information processing system, a recording medium, and an information processing method capable of acquiring a user's situation and notifying surroundings, and thereby encourage unobtrusive acts of kindness.

Solution to Problem

According to the present disclosure, there is provided a communication device including: a control unit that acquires current situation information of a first user based on an attribute of the first user and a current situation of the first user; and a communication unit that, in accordance with control by the control unit, transmits the current situation information of the first user to a surrounding communication device.

According to the present disclosure, there is provided an information processing system including: a storage unit that stores at least an attribute of a first user and an attribute of a second user; a communication unit that receives, from a first communication device, a current situation associated with the first user and generated current situation information, and receives, from a second communication device, a signal associated with the second user and indicating that the second communication device has received the current situation information from the first communication device; and a control unit that, on a basis of the attribute of the first user, the current situation information, and the attribute of the second user, controls a transmission of a signal to the second communication device determined to be capable of handling a situation of the first user indicated by the current situation information, the signal indicating that a user seeking handling from surroundings exists.

According to the present disclosure, there is provided an information processing system including: a storage unit that stores an attribute of a first user and attribute information of a specific object; a communication unit that receives, from a first communication device, identification information of a specific object disposed around the first user and identification information of the first user as a current situation associated with the first user; and a control unit that, in a case of determining that the first user is a user who needs to seek handling from surroundings on a basis of a relationship between the attribute of the first user and the attribute information of the specific object, controls a transmission to the first communication device via the communication unit of an indication of a need to seek handling from surroundings.

According to the present disclosure, there is provided a computer-readable recording medium on which a program is recorded, the program causing a computer to function as: a control unit that acquires current situation information of a first user based on an attribute of the first user and a current situation of the first user; and a communication unit that, in accordance with control by the control unit, transmits the current situation information of the first user to a surrounding communication device.

According to the present disclosure, there is provided an information processing method including: receiving, by a communication unit, from a first communication device, a current situation associated with a first user and generated current situation information, and receiving, from a second communication device, a signal associated with a second user and indicating that the second communication device has received the current situation information from the first communication device; and controlling, by a control unit, on a basis of an attribute of the first user stored in a storage unit, the received current situation information, and an attribute of the second user stored in the storage unit, a transmission of a signal to the second communication device determined to be capable of handling a situation of the first user indicated by the current situation information, the signal indicating that a user seeking handling from surroundings exists.

According to the present disclosure, there is provided an information processing method including: receiving, by a communication unit, from a first communication device, identification information of a specific object disposed around a first user and identification information of the first user as a current situation associated with the first user; and controlling, by a control unit, in a case of determining that the first user is a user who needs to seek handling from surroundings on a basis of a relationship between an attribute of the first user and attribute information of the specific object stored in a storage unit in association with the respective pieces of identification information, a transmission to the first communication device via the communication unit of an indication of a need to seek handling from surroundings.

Advantageous Effects of Invention

According to the present disclosure as described above, by acquiring a user's situation and notifying surroundings, it becomes possible to encourage unobtrusive acts of kindness.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
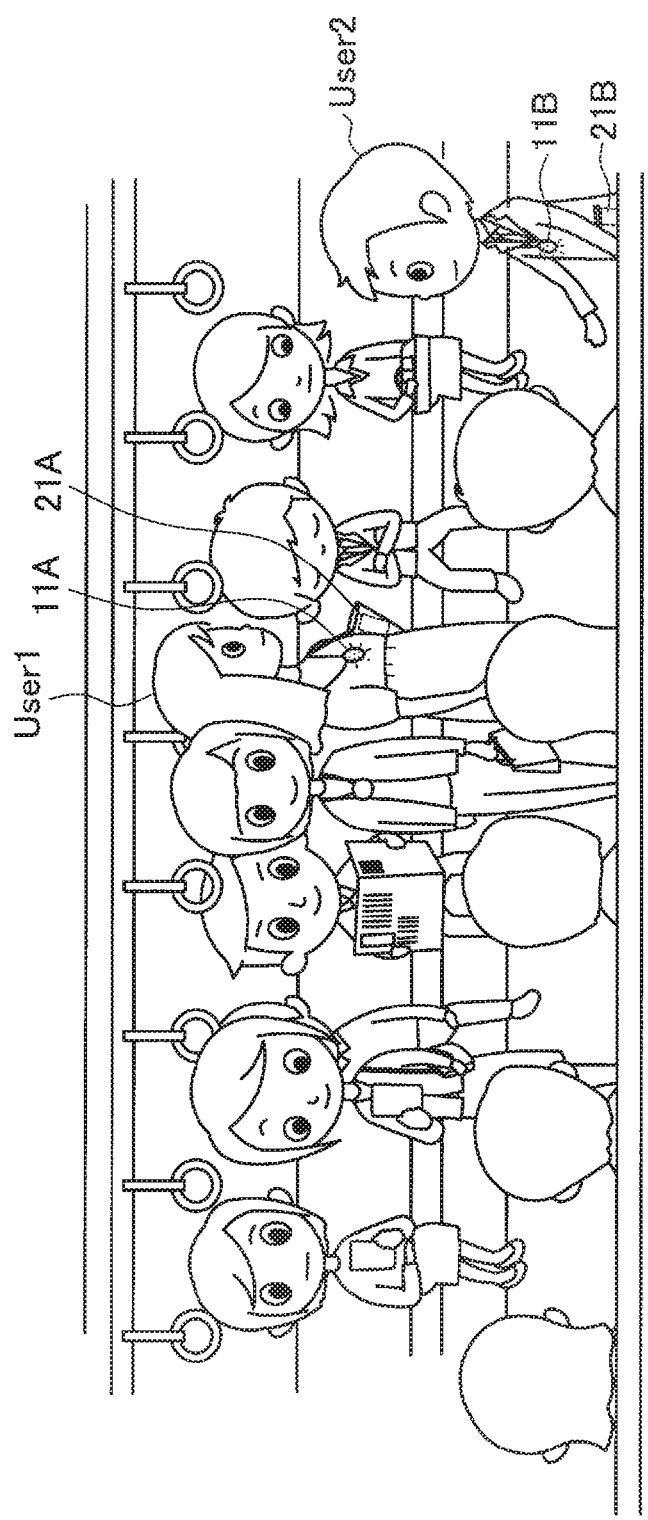
FIG. 1 is a diagram explaining an example of a scene where an act-of-kindness support system according to an embodiment of the present disclosure is applied.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. Overview of information processing system according to embodiment of present disclosure
2. Embodiments
2-1. First embodiment
2-1-1. Configuration of presentation device 11
2-1-2. Configuration of communication terminal 21
2-1-3. Operating process
2-1-4. Effects
2-2. Second embodiment
2-2-1. Configuration of communication terminal 22
2-2-2. Configuration of matching server 31
3. Applied examples
3-1. First applied example
3-1-1. Overview
3-1-2. Operating process
3-2. Second applied example
3-3. Third applied example
4. Conclusion 1. OVERVIEW OF ACT-OF-KINDNESS SUPPORT SYSTEM ACCORDING TO EMBODIMENT OF PRESENT DISCLOSURE An act-of-kindness support system (information processing system) according to an embodiment of the present disclosure is able to encourage unobtrusive acts of kindness by acquiring the situation of a person having trouble, and making that situation known to other people feeling kindness who are present around one. For example, the system is for enabling one to perform an unpretentious and unobtrusive act of kindness for a person in a troubled situation, such as giving up one's seat on a train to someone who is pregnant or injured, speaking to a tourist who is lost and trying to find someone who can speak English, or recognizing a child with a food allergy and being careful about what food to provide. Specifically, an act-of-kindness support system according to the present embodiment recognizes, on the basis of attributes of multiple preregistered users and a current situation (including action) of each user, whether or not one user is in a troubled situation, and also whether or not another user is capable of handling the situation. Additionally, the act-of-kindness support system can use light, vibration, text, graphics, or the like from a presentation device (such as a necklace-style device, a wristwatch-style device, or an armband-style device, for example) possessed by the user capable of handling the situation to unobtrusively notify that user of the presence of a person having trouble nearby, and thereby encourage an act of kindness.

As for the scene where an act-of-kindness support system according to the present embodiment is applied, consider being on a train as illustrated in FIG. 1, for example. On a train, in a case in which an elderly person, an injured person, a pregnant woman, or a person feeling ill is present, for example, wanting to give up one's seat is conceivable, but in cases in which the situation is difficult to judge definitively on sight, deciding whether or not to give up one's seat may be difficult in some cases. As illustrated in FIG. 1, in a case in which a User2 is sitting in a seat and thinking of giving up the seat to a person having trouble, User2 sometimes may be unable to decide on sight whether or not a nearby User1 is pregnant.

Accordingly, in the present embodiment, on the basis of an attribute "pregnant" of User1 and a current situation "standing inside a train" of User1, for example, if it is determined that User1 is currently in a troubled situation (needing help by being given a seat), a signal indicating that a nearby person wants someone to give up their seat is transmitted to a surrounding User2. Regarding the transmission of such a signal, by broadcasting to surrounding users by short-range communication such as Bluetooth (registered trademark) or Bluetooth Low Energy (BLE) from a communication terminal 21A carried inside a bag or the like of User1, for example, it is possible to ask for help from other people who are actually nearby. Note that BLE is more desirable from the standpoint of being able to broadcast (advertise) without the need for pairing. Also, the current situation of User1 may be sensed by sensors such as an acceleration sensor, a gyro sensor, a camera, or a microphone provided in a presentation device 11A or a communication terminal 21A of User1.

A communication terminal 21B carried inside a pocket or the like of User2 receives the above signal, and on the basis of an attribute "kindness: willing to give up seat on train" of User2 and a current situation "sitting inside a train" of User2, determines whether or not User2 is capable of handling the situation of "wanting someone to give up their seat". Next, in the case in which the communication terminal 21B determines that User2 is capable of handling the situation, a notification that a person around one is having trouble and wants someone to give up their seat is issued, the notification being issued by light, vibration, text, graphics, or the like from a presentation device 11B of User2. In the case in which a pendant-style presentation device 11B lights up or vibrates, for example, User2 can recognize that a person seeking help is present around one, look around for the person in question (in this case, a person wanting someone to give up their seat), notice and call out to the pregnant User1, and give up the seat. During this time, since a notification is issued by light, vibration, or the like only to persons able to perform an act of kindness, without issuing some kind of notification to other people on the train, only the persons involved can help each other naturally, without explicitly seeking help from everyone around. Also, if persons seeking help and persons able to help can be matched to encourage acts of kindness in this way, it becomes possible to increase happiness in society.

Note that in cases in which User2 looks around and is unable to find the person in question (including cases of being unsure of who the person in question is), it is also possible to issue a presence notification request to the person in question from the User2 side to the outside. Upon receiving such a request, the communication terminal 21A of User1 causes the presentation device 11A to vibrate, for example, thereby causing User1 to recognize that a kind person is around. With this arrangement, User1 can also be encouraged to look around and find User2. Additionally, by having the communication terminal 21A additionally cause the presentation device 11A to light up, it becomes possible to make User2 notice the presence of User1.

A specific exemplary configuration and operating process of an act-of-kindness support system according to an embodiment of the present disclosure described above will be described using the following embodiments. Note that although the communication terminal 21 and the presentation device 11 are described as being separate, this is only one example, and a user may also carry a communication device that integrates the communication terminal 21 and the presentation device 11.

2. EMBODIMENTS

2-1. First Embodiment

Figure 2:
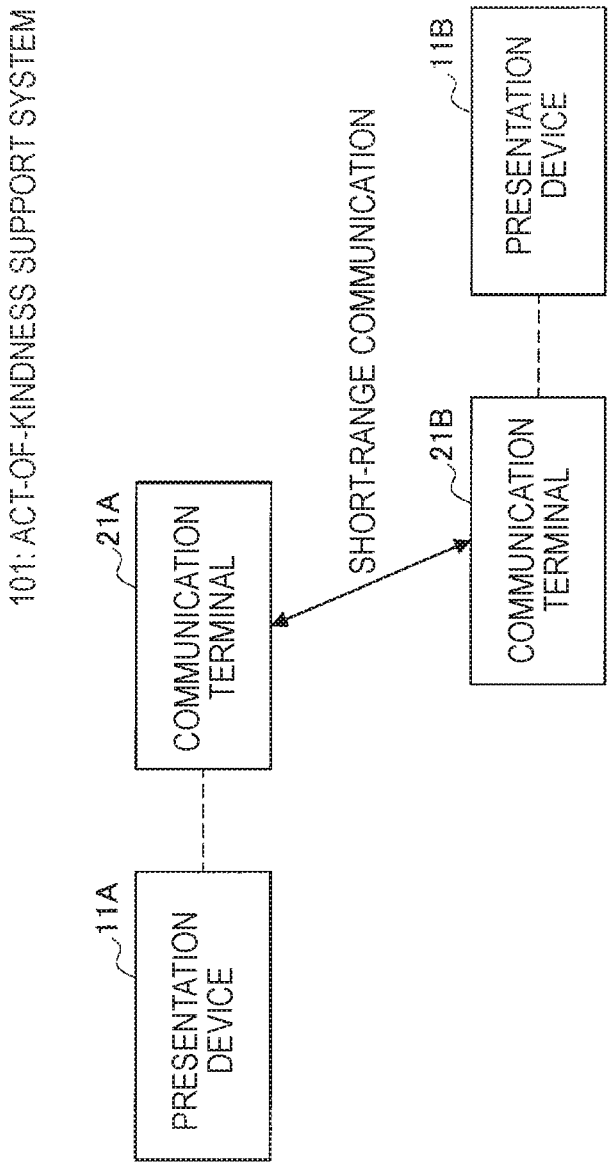
FIG. 2 is a diagram illustrating an exemplary overall configuration of an act-of-kindness support system according to the first embodiment.

First, an overall configuration of an act-of-kindness support system according to the first embodiment will be described with reference to FIG. 2. FIG. 2 is a diagram illustrating an exemplary overall configuration of an act-of-kindness support system 101 according to the present embodiment. As illustrated in FIG. 2, the act-of-kindness support system 101 according to the first embodiment connects a communication terminal 21A and a communication terminal 21B by short-range communication, and in addition, the communication terminal 21A connects to and controls presentation on a presentation device 11A, while the communication terminal 21B connects to and controls presentation on a presentation device 11B. The communication terminal 21 is anticipated to be a terminal such as a smartphone, a mobile phone, a tablet, or a personal computer (PC). The presentation device 11 is anticipated to be a device such as a necklace-style device, a watch-style device, an armband-style device, a glasses-style device, a badge-style device, or an earring-style device. The communication terminal 21 and the presentation device 11 are connected by wireless communication such as Bluetooth (registered trademark), Bluetooth Low Energy (BLE), or Wi-Fi (registered trademark), for example, and data may be transmitted and received. Note that although the communication terminal 21 and the presentation device 11 are taken to be separate devices herein, the present embodiment is not limited thereto, and these devices may also be integrated. In this case, the processing functions of the presentation device 11 are implemented as an application of the communication terminal 21, and a notification may be issued by graphics on a screen, for example.

2-1-1. Configuration of Presentation Device 11

Figure 3:
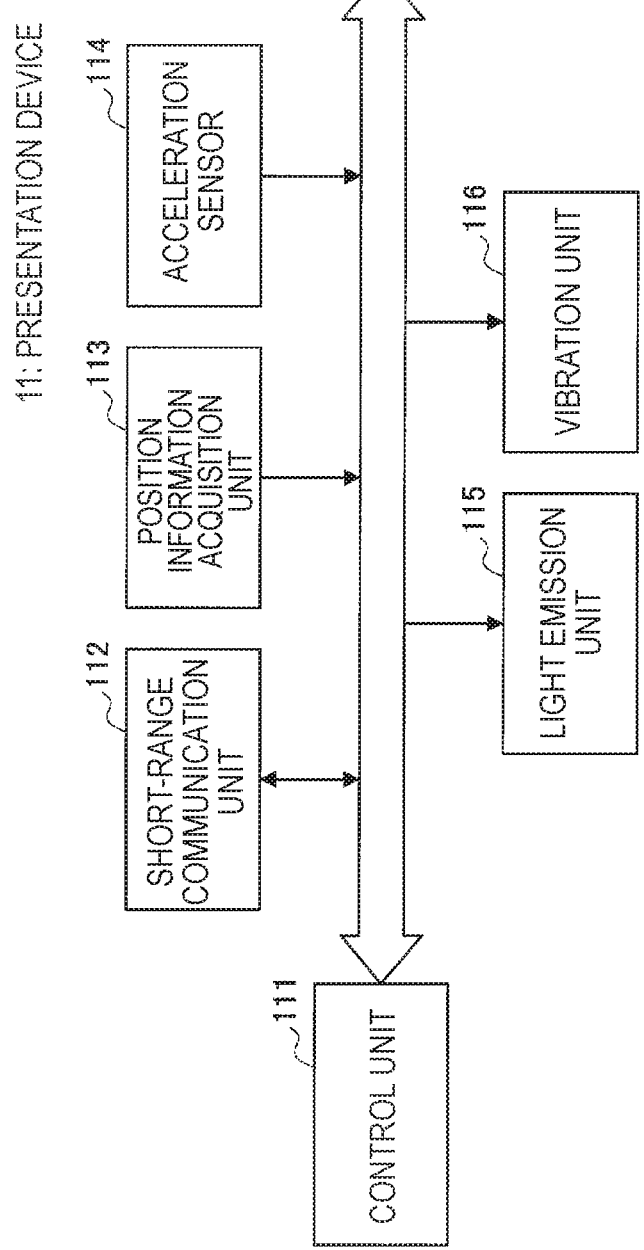
FIG. 3 is a block diagram illustrating an exemplary configuration of a presentation device according to the present embodiment.

FIG. 3 is a block diagram illustrating an exemplary configuration of a presentation device 11 according to the first embodiment. As illustrated in FIG. 3, the presentation device 11 includes a control unit 111, a short-range communication unit 112, a position information acquisition unit 113, an acceleration sensor 114, a light emission unit 115, and a vibration unit 116.

The control unit 111 functions as a computational processing device and control device, and controls overall operation inside the presentation device 11 by following various programs. The control unit 111 is realized by an electronic circuit such as a central processing unit (CPU) or a microprocessor, for example. In addition, the control unit 111 may also include read-only memory (ROM) that stores information such as programs to use and computational parameters, as well as random access memory (RAM) that temporarily stores information such as parameters that change as appropriate.

Also, the control unit 111 controls the transmission of information detected by the position information acquisition unit 113 and the acceleration sensor 114 (specifically position information and acceleration information) to the communication terminal 21 via the short-range communication unit 112. Also, the control unit 111 executes control of the lighting up/turning off of the light emission unit 115 and control of the vibration by the vibration unit 116, by following a control signal received from the communication terminal 21 via the short-range communication unit 112 (specifically, a presentation control signal by a presentation control unit 2114 described later).

The short-range communication unit 112 is a communication module that includes a wireless communication antenna, and realizes the wireless transmission and reception of data with the communication terminal 21 existing a short distance away. Additionally, the short-range communication unit 112 is realized by wireless communication such as Bluetooth (registered trademark), Bluetooth Low Energy (BLE), or Wi-Fi (registered trademark), for example.

The position information acquisition unit 113 includes a function of acquiring position information about the presentation device 11. For example, the position information acquisition unit 113 may be a Global Positioning System (GPS) antenna and a GPS processing unit that processes GPS signals received by the GPS antenna. Alternatively, the position information acquisition unit 113 may be a Wi-Fi antenna that receives Wi-Fi radio waves from multiple base stations, and a position computation unit that estimates the distances to each base station from the received signal strength of the Wi-Fi radio waves, and utilizes the distance to each base station and the position of each base station to compute a current position on the basis of the triangulation principle.

The acceleration sensor 114 is a sensor that detects acceleration as a voltage value. The acceleration sensor 114 may be a 3-axis acceleration sensor that respectively detects acceleration in an X-axis direction, acceleration in a Y-axis direction, and acceleration in a Z-axis direction, for example. In the example illustrated in FIG. 3, a configuration that includes only the acceleration sensor 114 is given, but the present embodiment is not limited thereto, and the presentation device 11 may also include at least one of a gyro sensor (a type of measuring instrument that detects the angle and angular velocity of an object) and a geomagnetic sensor (a sensor that detects geomagnetism as a voltage value) instead of, or in addition to, the acceleration sensor 114. These sensors are used when performing action recognition (recognition of postures such as "sitting, standing", and movements such as "walking, running").

The light emission unit 115 is an example of a notification unit that uses light to notify the user and surroundings. The light emission unit 115, under control by the control unit 111, controls the turning on/off of the light source, the brightness, blinking, the emitted color, and the like.

The vibration unit 116 is an example of a notification unit that uses vibration to notify the user and surroundings. The vibration unit 116, under control by the control unit 111, controls the turning on/off of vibration, the strength of vibration, the vibration pattern, and the like.

The above thus specifically describes a configuration of the presentation device 11 according to the present embodiment. Note that the configuration illustrated in FIG. 3 is one example, and the present embodiment is not limited thereto. For example, the presentation device 11 may also include a speaker or a display unit as an example of a notification unit. In addition, the presentation device 11 may also include a physical button, switch, pressure sensor, or the like for detecting operation input by the user as an input unit. In addition, the presentation device 11 may also include components such as a biological sensor that senses biological information about the user (such as pulse, heartbeat, blood pressure, body temperature, amount of perspiration, or brain waves), an environment sensor that senses information about the surrounding environment (such as air temperature, barometric pressure, humidity, wind force, or illuminance), a miniature camera capable of imaging the user's expression or the surrounding state, or a microphone capable of picking up the user's voice or sounds from the surrounding environment. Biological information about the user and information about the surrounding environment is used together with the above position information and acceleration information, for example, when a "situation information generation unit 2111" described later determines whether or not there is a situation in which one needs help.

Also, a portion of the configuration included in the presentation device 11 may also be provided in the communication terminal 21. For example, the position information acquisition unit 113 or the acceleration sensor 114 may also be provided in the communication terminal 21.

2-1-2. Configuration of Communication Terminal 21

Figure 4:
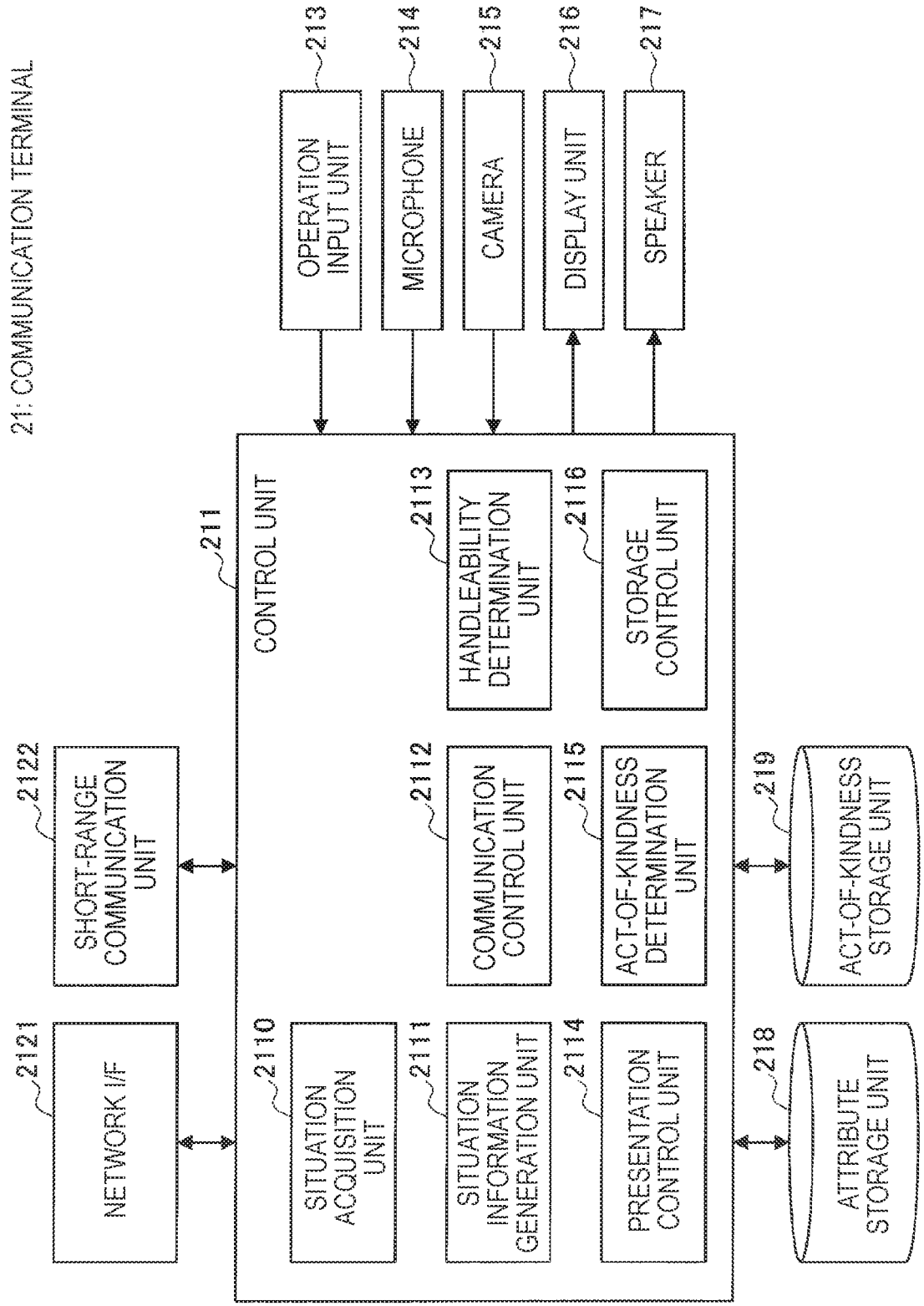
FIG. 4 is a block diagram illustrating an exemplary configuration of a communication terminal according to the present embodiment.

FIG. 4 is a block diagram illustrating an exemplary configuration of a communication terminal 21 according to the present embodiment. As illustrated in FIG. 4, the communication terminal 21 includes a control unit 211, a network interface (I/F) 2121, a short-range communication unit 2122, an operation input unit 213, a microphone 214, a camera 215, a display unit 216, a speaker 217, an attribute storage unit 218, and an act-of-kindness storage unit 219.

The control unit 211 functions as a computational processing device and control device, and controls overall operation inside the communication terminal 21 by following various programs. The control unit 211 is realized by an electronic circuit such as a CPU or a microprocessor, for example. In addition, the control unit 211 may also include ROM that stores information such as programs to use and computational parameters, as well as RAM that temporarily stores information such as parameters that change as appropriate.

Also, as illustrated in FIG. 4, the control unit 211 functions as a situation acquisition unit 2110, a situation information generation unit 2111, a communication control unit 2112, a handleability determination unit 2113, a presentation control unit 2114, an act-of-kindness determination unit 2115, and a storage control unit 2116.

The situation acquisition unit 2110 acquires the user's current situation, on the basis of various sensor data. Specifically, for example, the situation acquisition unit 2110 performs user action recognition on the basis of position information and/or acceleration information received from the presentation device 11 via the short-range communication unit 2122, as well as audio data and video data acquired from the microphone 214 and/or the camera 215 of the communication terminal 21 (or a microphone and camera provided in the presentation device 11), and acquires the action recognition result as the user's current situation. With action recognition, postures such as "sitting, standing", movements such as "walking, running", and states such as "on a bicycle, on a train" are recognized.

The situation information generation unit 2111 includes a function of generating information about the user's current situation, on the basis of user attributes and the user's current situation (action recognition result). User attributes are stored in the attribute storage unit 218, for example. Herein, the user attributes stored in the attribute storage unit 218 includes difficulty attributes by which troubles and handicaps for the user can be specified, or kindness attributes by which acts of kindness and abilities that the user is able to perform can be specified. An ID is assigned to each attribute, and in addition, multiple difficulty attribute IDs or kindness attribute IDs may be associated with a single user. Also, both difficulty attributes and kindness attributes may be associated with the same person. Anticipated difficulty attributes are, for example, being pregnant, being injured, feeling unwell, being lost, or having an allergy. Such attributes may be registered by the user him- or herself, or in the case of an illness or allergy, for example, the attribute may be registered by the doctor making the diagnosis. Also, anticipated kindness attributes are, for example, actively wanting to give up one's seat, wanting to help carry heavy luggage, being proficient in sign language, being proficient in a foreign language, having medical knowledge, or carrying a large amount of small change.

Additionally, the "information about the user's current situation" generated by the situation information generation unit 2111 indicates an action currently desired by the user (specifically, the content of needed help) determined on the basis of the combination of the user's attributes and the user's current situation. In the case in which User1's attribute is "pregnant" and User1's current situation is "standing inside a train", for example, the situation information generation unit 2111 generates situation information (that is, context) indicating "a situation of wanting someone to give up their seat (a situation of wanting to sit down)". What kind of situation information is to be generated for what combinations of attributes and situations may be registered in advance, or acquired by machine learning.

The communication control unit 2112 controls the transmission and reception of data with an external device by the network I/F 2121 and the short-range communication unit 2122. For example, the communication control unit 2112 transmits situation information about User1 generated by the situation information generation unit 2111 to another communication terminal around (existing a short distance away) via the short-range communication unit 2122. At this point, the communication control unit 2112 may also transmit situation information about User1 to one or more other communication terminals 21 around by BLE broadcasting, for example. In addition, the communication control unit 2112 is also capable of transmitting a presentation control signal to the presentation device 11 of the user from the short-range communication unit 2122.

The handleability determination unit 2113 determines, on the basis of situation information transmitted from another communication terminal, the kindness attributes of the user, and the current situation of the user, whether or not the user is capable of handling the situation indicated by the situation information (that is, whether or not the user is able to help). For example, in the case in which the situation information is "a situation of wanting someone to give up their seat", a kindness attribute of User2 is "actively wants to give up one's seat", and the situation of User2 is "sitting down", the handleability determination unit 2113 determines that the situation is "handleable".

The presentation control unit 2114 controls the presentation of various information to the user (notification control). For example, the presentation control unit 2114 is able to control information presentation by an image and sound from the display unit 216 and the speaker 217, and information presentation by light and vibration from the light emission unit 115 and the vibration unit 116 of the presentation device 11 connected via the short-range communication unit 2122. Specifically, in the case in which the handleability determination unit 2113 determines that User2 is capable of handling a situation, the presentation control unit 2114 controls light emission/vibration of the presentation device 11 of the user via the short-range communication unit 2122. With this arrangement, the user can recognize that a person having trouble is around one. Also, in the case of receiving a signal indicating that a situation is handleable from a surrounding communication terminal, the presentation control unit 2114 controls vibration of the presentation device 11 of the user via the short-range communication unit 2122. With this arrangement, the user understands that a kind person who is going to help the user is around. Additionally, in the case in which a presence notification request is issued to the outside from a surrounding communication terminal, the presentation control unit 2114 may obtain user approval (or in the case in which approval is obtained in advance) and control light emission of the presentation device 11 of the user via the short-range communication unit 2122.

The act-of-kindness determination unit 2115 determines whether or not an act of kindness has been performed. For example, the act-of-kindness determination unit 2115 determines whether or not a user has performed an act of kindness for a target user, on the basis of a change in the situation of the target user (specifically, a change in the action recognition result) received from another communication terminal via the short-range communication unit 2122), and a change in the situation of the user acquired by the situation acquisition unit 2110. For example, in the case in which the user stands up and the target user sits down, the act-of-kindness determination unit 2115 can determine that the user has given up his or her seat to the target user (performed an act of kindness). At this point, the act-of-kindness determination unit 2115 may also determine whether or not an act of kindness has been performed by additionally determining that both situation changes have occurred within a certain amount of time, and both are within a certain distance.

Additionally, the act-of-kindness determination unit 2115 may also determine that an act of kindness has been performed on the basis of information that is input explicitly and manually by the user or the target user.

The storage control unit 2116 controls operations such as the registration, updating, and removal of information in the attribute storage unit 218 and the act-of-kindness storage unit 219. For example, in the case in which the act-of-kindness determination unit 2115 determines that an act of kindness has been performed, the storage control unit 2116 controls the storage of information about the act of kindness in the act-of-kindness storage unit 219.

At this point, as the information about the act of kindness, the act-of-kindness storage unit 219 records the time and place at which the act of kindness is performed and the content of the act of kindness in association with the ID of the person who performed the act of kindness and/or the ID of the person who received the act of kindness.

The network interface (I/F) 2121 connects to and transmits or receives information with an external device over a network. For example, in the case in which the attribute storage unit 218 and the act-of-kindness storage unit 219 are in the cloud, the communication terminal 21 performs operations such as the acquisition of user attributes and the registration of an act of kindness over a network.

The short-range communication unit 2122 connects to an external device existing around one, and transmits or receives information. For example, the short-range communication unit 2122 connects to another communication terminal 21 existing around one or to a presentation device 11 worn by the user, and transmits or receives information. Also, the short-range communication unit 2122 may be realized by wireless communication such as Bluetooth, BLE, or Wi-Fi.

The operation input unit 213 is realized by components such as switches, buttons, or a touch panel, and detects operation input by the user, and output detected input information to the control unit 211.

The microphone 214 picks up the user's voice or environmental sounds, converts the sound into an audio signal (such as by digital conversion and encoding), and outputs to the control unit 211. An audio signal acquired by the microphone 214 is used by the situation acquisition unit 2110 to recognize the user's situation (such as whether the user is on a train, outdoors/indoors, or at work/school), for example.

The camera 215 images the user's face or the surrounding environment, and outputs a captured image to the control unit 211. A captured image acquired by the camera 215 is used by the situation acquisition unit 2110 to recognize the user's situation (such as whether the user is on a train, outdoors/indoors, or at work/school), for example.

The display unit 216 is an example of an output device, and may be a display device such as a liquid crystal display (LCD) device or an organic EL (organic light-emitting diode (OLED)) display device. The display unit 216 can provide the user with information by displaying the information on a screen.

The speaker 217 can convert an audio signal supplied from the control unit 211 (such as by decoding and analog conversion) and output audio.

The above thus specifically describes a configuration of the communication terminal 21 according to the present embodiment. Note that the configuration illustrated in FIG. 4 is one example, and the present embodiment is not limited thereto. For example, the communication terminal 21 is not required to have all of the components illustrated in FIG. 4, and may also be configured to lack a portion thereof, for example, or a portion may exist in the presentation device 11 or the cloud, and may be connected by the short-range communication unit 2122 or the network I/F 2121. In addition, the communication terminal 21 may also include an action history storage unit that stores the user's actions periodically (or when the action changes). For example, the position of the user at a certain time (position information from GPS or Wi-Fi positioning), a place (a place category such as park, train, outdoors, work, or school), and an action (such as standing, sitting, or moving (types of transportation)) are stored.

2-1-3. Operating Process

Next, an operating process according to the present embodiment will be described with reference to FIGS. 5 and 6. Herein, as an example, kindness support will be described for when a pregnant woman (first user, attribute: pregnant) and a kind person (second user, attribute: actively wants to give up one's seat) are present together on a train.

Figure 5:
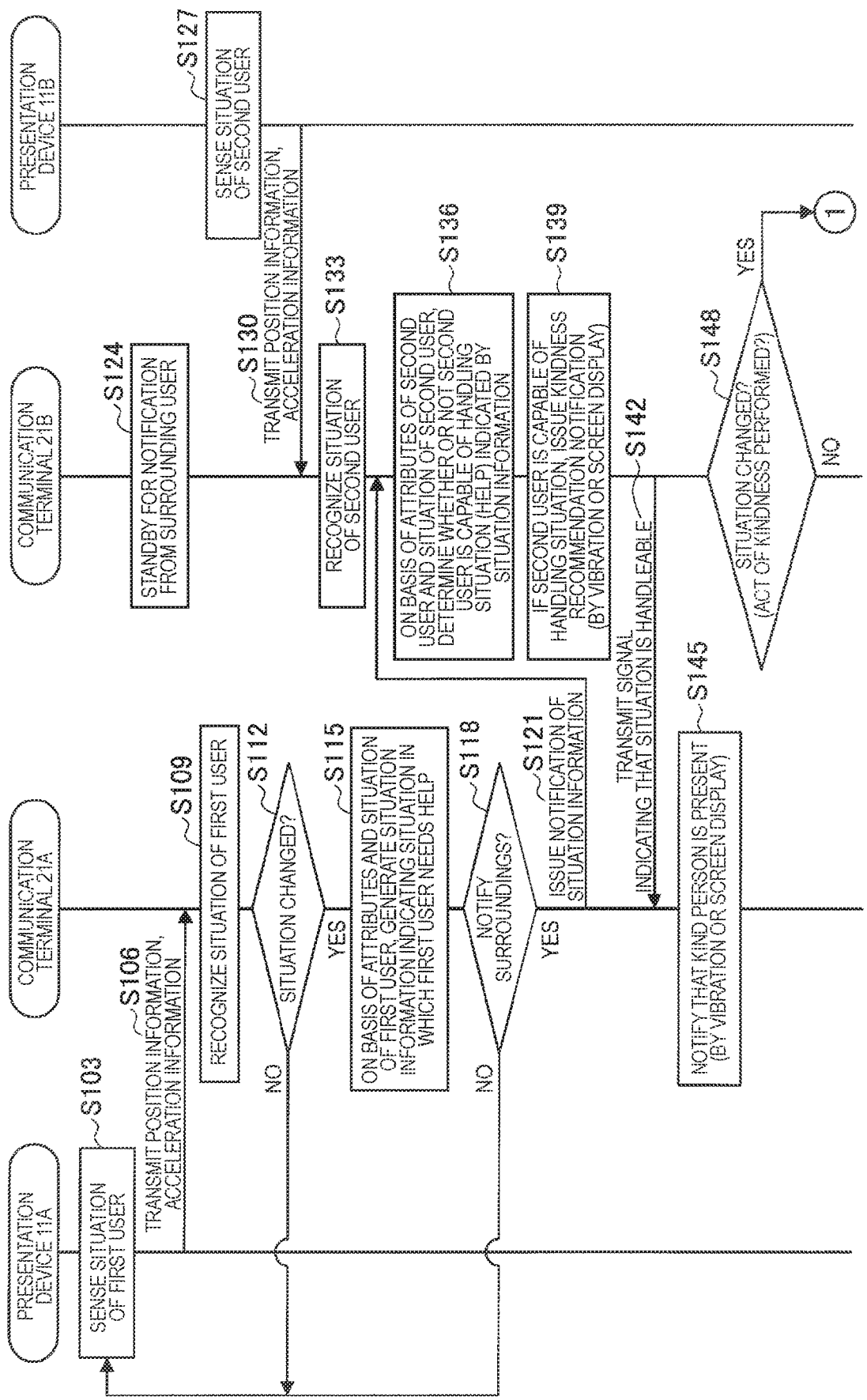
FIG. 5 is a sequence diagram illustrating an operating process of an act-of-kindness support system according to the present embodiment.
Figure 6:
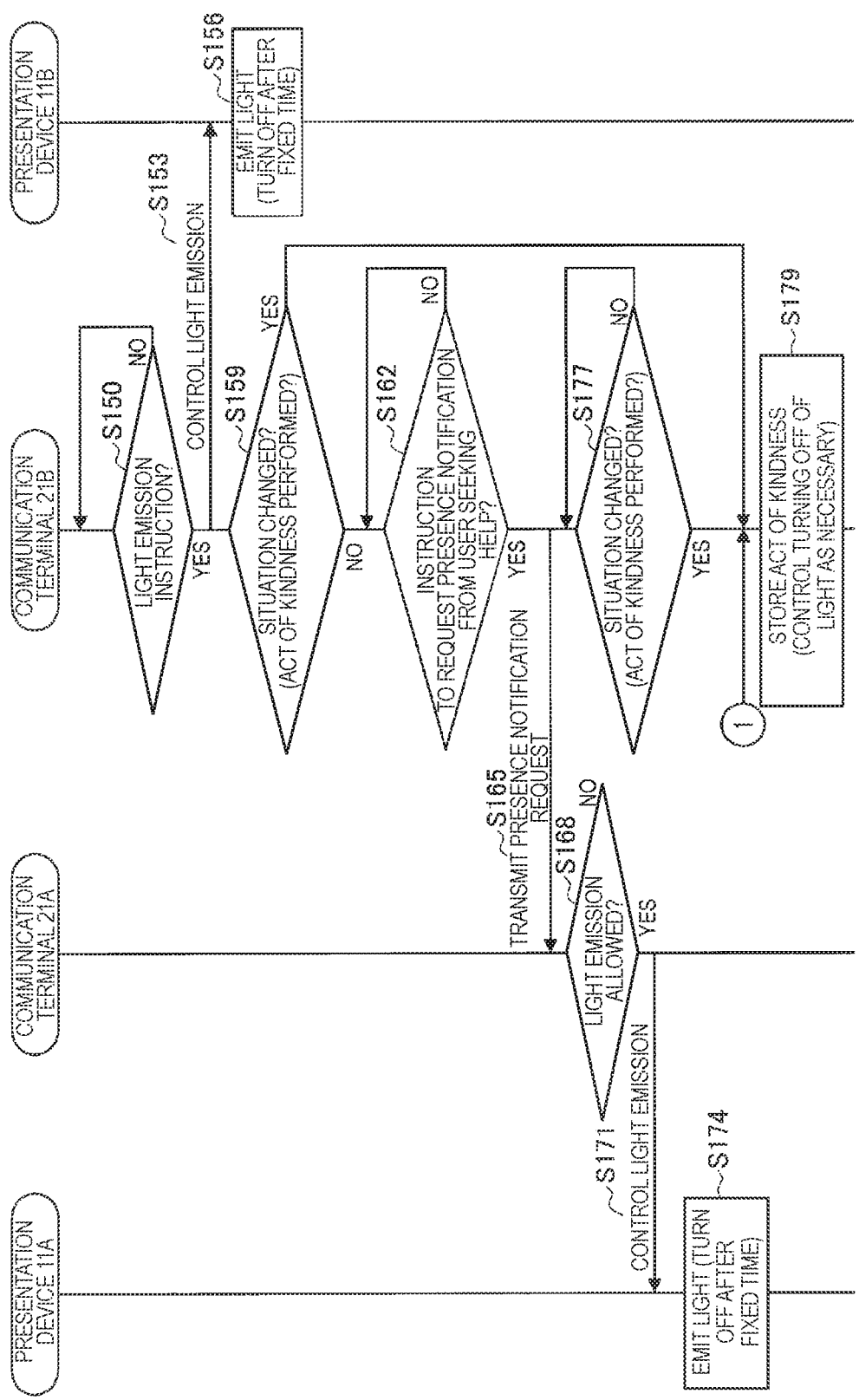
FIG. 6 is a sequence diagram illustrating an operating process of an act-of-kindness support system according to the present embodiment.

FIGS. 5 and 6 are sequence diagrams illustrating an operating process of an act-of-kindness support system according to the first embodiment. As illustrated in FIG. 5, first, the presentation device 11A of the first user senses the situation (action) of the first user with the position information acquisition unit 113 and the acceleration sensor 114 (step S103), and transmits acquired position information and acceleration information (as well as the time) to the communication terminal 21A with the short-range communication unit 112 (step S106).

Next, the communication terminal 21A of the first user conducts situation recognition (action recognition) of the first user with the situation acquisition unit 2110 (step S109), and determines whether or not the situation has changed (step S112). Specifically, it is determined whether or not a change of action has occurred, such as the first user getting on a train, getting off a train, sitting down, or standing up, for example.

Next, in the case in which the situation has changed (step S112/Yes), the situation information generation unit 2111 determines whether or not there is a situation in which help is needed, on the basis of the attributes and the situation (action) of the first user, and in the case of a situation in which help is needed, the situation information generation unit 2111 generates situation information indicating that the first user is in a situation in which help is needed (step S115). In the case of determining that there is not a situation in which help is needed, the generation of situation information is not conducted. Also, the attributes of the first user are preregistered in the attribute storage unit 218.

Next, the communication control unit 2112 determines whether or not to notify surroundings (step S118). Whether or not to notify surroundings may be set in advance by the first user. Cases such as a setting to notify always, a setting that requires user approval every time, and a setting in which whether or not to notify depends on the situation are anticipated.

Subsequently, in the case of notifying surroundings (step S118/Yes), the communication control unit 2112 notifies one or more surrounding communication terminals 21 of the generated situation information (step S121).

Meanwhile, the communication terminal 21B of the second user is in a state of standing by for a notification from a surrounding user (step S124). Additionally, the presentation device 11B of the second user periodically senses the situation of the second user (step S127), and transmits position information and acceleration information about the second user (as well as the time) to the communication terminal 21B (step S130). Subsequently, the situation acquisition unit 2110 of the communication terminal 21B conducts situation recognition of the second user (step S133).

Next, when the communication terminal 21B receives a situation notification from the communication terminal 21A, the handleability determination unit 2113 determines whether or not the second user is capable of handling the situation (help) indicated by the situation information, on the basis of the attributes of the second user and the situation (action) of the second user (step S136).

Next, in the case in which the second user is capable of handling the situation, the presentation control unit 2114 of the communication terminal 21B controls the issuing of a kindness recommendation notification to the second user (step S139). Specifically, the presentation control unit 2114 displays a screen indicating "A person around you wants someone to give up their seat." on the display unit 216 of the communication terminal 21B and causes the presentation device 11B to vibrate, for example. With this arrangement, the second user is able to recognize that a person around one wants someone to give up their seat, look around and visually find the target user, and give up one's seat. In this way, by notifying the second user with vibration and a screen display without specifying who the target user is (an attribute of the target user (for example, "pregnant") may be presented), an unobtrusive act of kindness can be encouraged without being known by surrounding people. Note that it is also possible to issue a notification to the second user with sound from the speaker 227, as long as the sound is very quiet. Alternatively, in the case in which the speaker 227 has directionality, it is possible for the presentation control unit 2114 to issue a notification with sound controlled so that only the second user can hear the sound.

Subsequently, the communication control unit 2112 of the communication terminal 21B controls the transmission of a signal indicating that the situation is handleable to the communication terminal 21A (step S142).

Next, the communication terminal 21B notifies the first user with vibration and a screen display that a kind person is around one (step S145). With this arrangement, the first user is able to briefly look around or the like, and accept the kindness of the second user more easily.

Subsequently, the communication terminal 21B uses the act-of-kindness determination unit 2115 to determine whether or not the situation (action) of the second user has changed, or in other words, whether or not an act of kindness has been performed (step S148). For example, in the case in which the second user receiving the kindness recommendation notification on a train changes from a sitting state to a standing state, the act-of-kindness determination unit 2115 determines that an act of kindness (giving up one's seat) has been performed.

Next, in the case in which the situation of the second user has not changed (step S148/No), in accordance with a light emission instruction from the second user (step S150/Yes), the communication terminal 21B causes the presentation device 11B to emit light (steps S153, S156). In other words, in the case in which the second user looks around but is unable to find the target user (or is unsure of whether a person is pregnant), and is unable to given up the seat, the second user taps a light emission button displayed on the screen of the communication terminal 21B or pushes a light emission button provided on the presentation device 11B, thereby causing light to be emitted from the presentation device 11B that the second user is wearing, and enabling the other person (herein, the first user) to notice one's presence. The light emission of the presentation device 11B is turned off after a fixed time, for example.

In the case in which the users still do not notice each other and the second user is unable to give up the seat (that is, in the case in which the situation of the second user does not change (step S159/No)), the second user is able to request a presence notification from the user seeking help (step S162). For example, the second user taps an "external presence notification request button" displayed on the screen of the communication terminal 21B or performs a long-press on a specific button on the presentation device 11B, and thereby inputs an instruction to request a presence notification to the outside.

Subsequently, in the case in which there is an instruction for a presence notification request from the second user (step S162/Yes), the communication control unit 2112 of the communication terminal 21B controls the transmission of a presence notification request to the communication terminal 21A via the short-range communication unit 2122 (step S165).

Next, in the case in which light emission is allowed (step S168/Yes), the presentation control unit 2114 of the communication terminal 21A controls, via the short-range communication unit 2122, light emission from the presentation device 11A worn by the first user (steps S171, S174). The allowing of light emission may be allowed by the first user in advance, or approval may be obtained from the first user every time (for example, a light emission allow/deny button is displayed on the display unit 216). In this way, by ultimately also causing the presentation device 11A of the first user to emit light, the second user has a higher probability of finding the first user, and an act of kindness can be supported. The light emission of the presentation device 11A is turned off after a fixed time, for example.

Subsequently, in the case in which the act-of-kindness determination unit 2115 determines that an act of kindness has been performed (that is, the situation has changed) (step S177/Yes, S159/Yes, S148/Yes), the communication terminal 21B uses the storage control unit 2116 to control the storage of information related to the act of kindness (such as the time, place, and content) in the act-of-kindness storage unit 219. Note that the storage of an act of kindness may also be conducted in the communication terminal 21A on the first user side. In this case, the time, place, and what type of kindness was received, for example, are stored as the information related to the act of kindness.

2-1-4. Effects

The above thus specifically describes an act-of-kindness support system according to the first embodiment. According to the present embodiment, a person needing help and a person wanting to perform an act of kindness are matched to each other, thereby lowering the hurdle to performing daily acts of kindness (that is, reducing hesitation about whether to perform an act of kindness), and increasing the opportunity to perform acts of kindness. By this arrangement, trust relationships can be strengthened among people living in social life, and the base level of happiness in society as a whole can be raised.

Also, in the present embodiment, on-the-spot kindness is supported in the case of persons who happen to be present a physically short distance away from each other, and unlike text-based kindness or words of appreciation over a network, kindness in the real world that resonates strongly can be recommended further.

Also, by issuing unobtrusive notifications using light, vibration, text, graphics, or sound so that persons can recognize each other in a state of being present and visible to each other a short distance away, acts of kindness can be induced naturally. Furthermore, by unobtrusively notifying the matched user (the user determined to be capable of handling a situation), without explicitly requesting users who are unable to handle the situation, it is possible for only the persons involved to understand the situation and perform an act of kindness naturally.

2-2. Second Embodiment

In the first embodiment above, an act-of-kindness support system is executed by an exchange between the terminals of a first user and a second user (specifically, the communication terminal 21A and the communication terminal 21B) without going through a server, but the present disclosure is not limited thereto, and may also be an act-of-kindness support system that includes a matching server, for example. In this case, it is possible to control whether to issue a kindness recommendation notification preferentially to someone in cases in which multiple kind persons are present. Hereinafter, such an act-of-kindness support system that includes a matching server will be described as a second embodiment.

Figure 7:
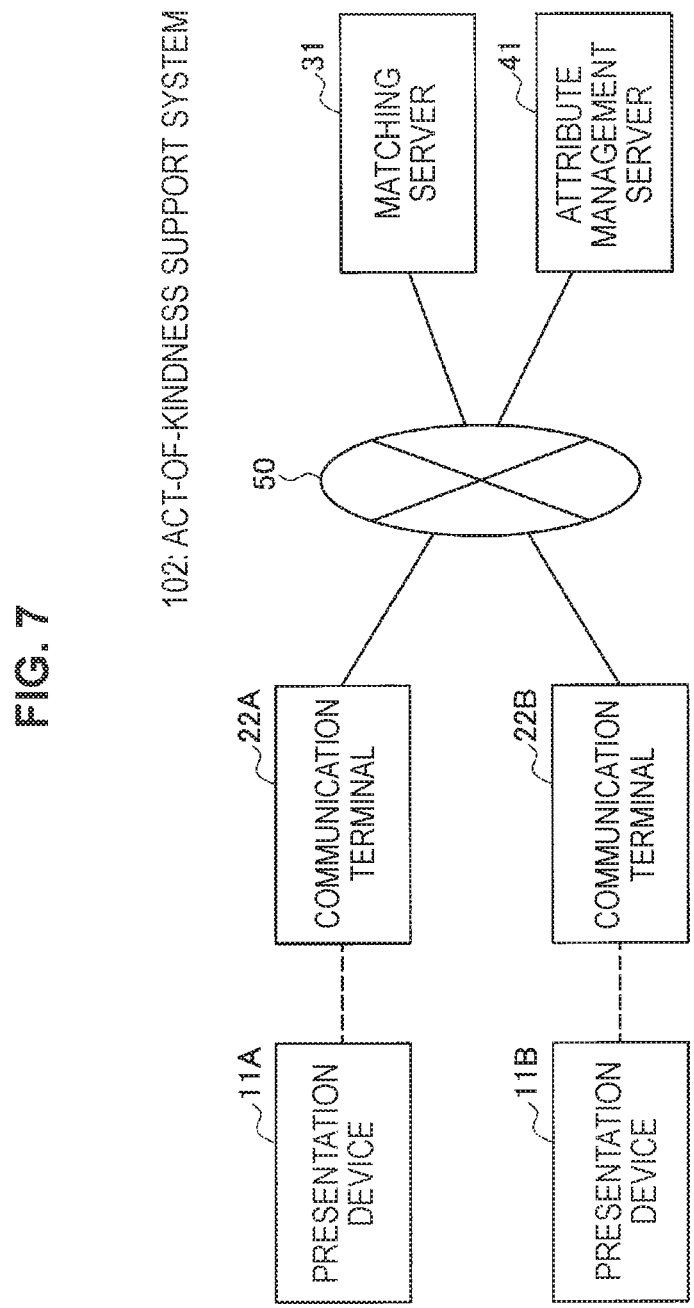
FIG. 7 is a diagram illustrating an exemplary overall configuration of an act-of-kindness support system according to the second embodiment.

FIG. 7 is a diagram illustrating an exemplary overall configuration of an act-of-kindness support system 102 according to the second embodiment. As illustrated in FIG. 7, the act-of-kindness support system 102 includes communication terminals 22A and 22B, and a matching server 31. The communication terminals 22A and 22B and the matching server 31 are connected via a network 50. Also, the communication terminal 22 (this term hereinafter collectively designating the communication terminals 22A and 22B when it is not necessary to distinguish the two) is connected to a presentation device 11 (this term hereinafter collectively designating the presentation devices 11A and 11B when it is not necessary to distinguish the two) by short-range communication such as BLE. Also, the matching server 31 connects to an attribute management server 41 via the network 50, and is able to acquire the attributes of a preregistered target user.

The attribute management server 41 manages the attributes of persons. For example, an ID is assigned personally to each person and associated with a difficulty attribute ID by which that person's troubles or handicaps can be specified, or a kindness attribute ID by which what types of kindness and what types of abilities that person has can be specified. Multiple difficulty attribute IDs and kindness attribute IDs may also be associated with a personal ID.

Also, an action management server (not illustrated) additionally may be provided on the network 50. In the action management server, daily actions of each user (what types of actions are performed when and where) are stored in association with a user ID.

With the act-of-kindness support system 102 having the above configuration, in the matching server 31, a user capable of handling a situation indicated by situation information transmitted from one communication terminal 22 is matched from among other communication terminals 22 existing around that communication terminal 22, and the selected communication terminal 22 is informed that a person around one is having trouble to encourage an act of kindness. At this point, in the case in which multiple users capable of handling the situation are present, the matching server 31 is able to control the issuing of a kindness recommendation notification to a certain number of high-ranking users ranked in accordance with an order of priority.

Hereinafter, the configuration of each device included in such an act-of-kindness support system 102 will be described specifically with reference to FIGS. 8 and 9. Note that since the configuration of the presentation device 11 according to the present embodiment is similar to the first embodiment described with reference to FIG. 3, the description will be reduced or omitted herein.

2-2-1. Configuration of Communication Terminal 22

Figure 8:
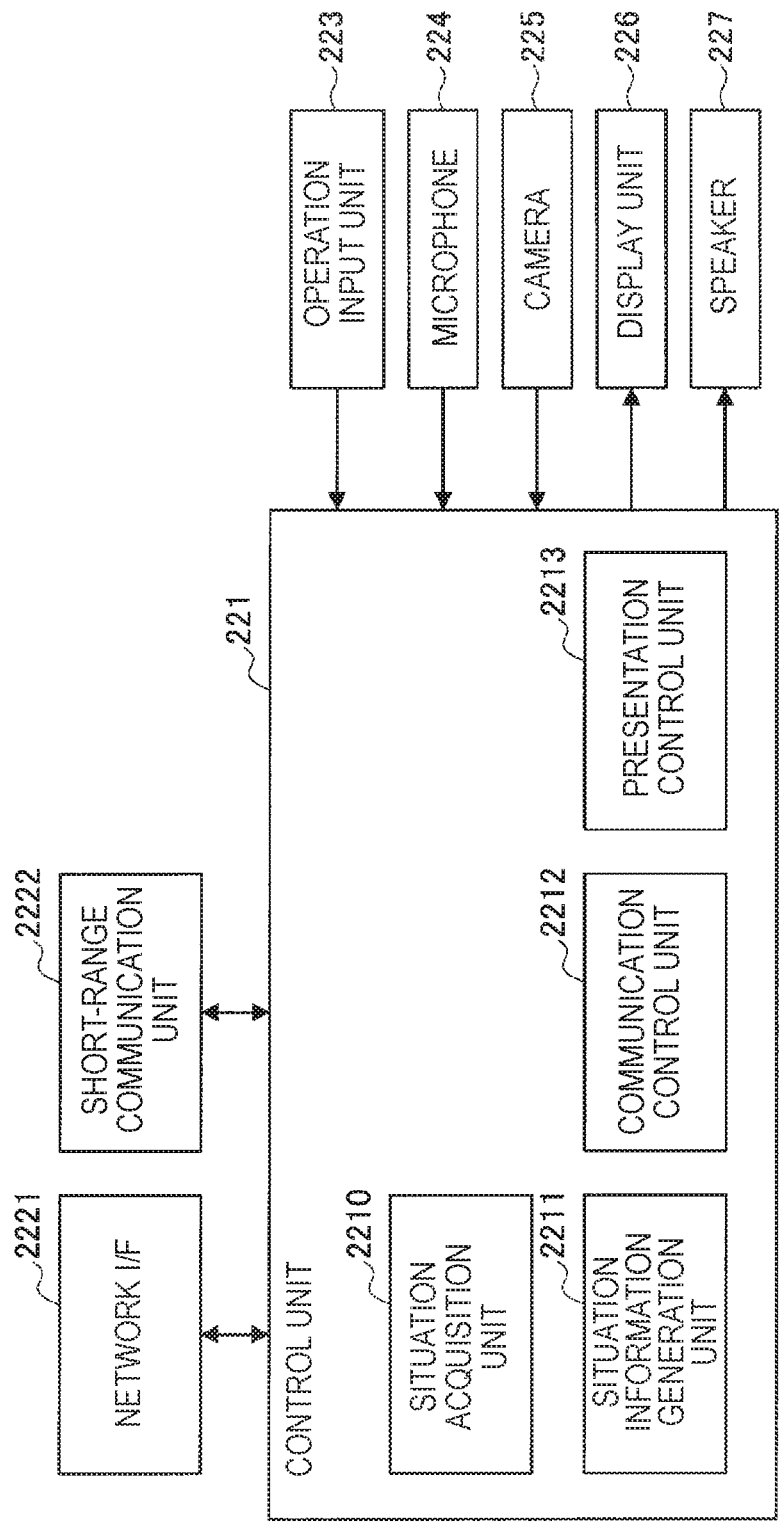
FIG. 8 is a block diagram illustrating an exemplary configuration of a communication terminal according to the present embodiment.

FIG. 8 is a block diagram illustrating an exemplary configuration of a communication terminal 22 according to the second embodiment. As illustrated in FIG. 8, the communication terminal 22 includes a control unit 221, a network I/F 2221, a short-range communication unit 2222, an operation input unit 223, a microphone 224, a camera 225, a display unit 226, and a speaker 227. Also, the control unit 221 functions as a situation acquisition unit 2210, a situation information generation unit 2211, a communication control unit 2212, and a presentation control unit 2213.

Each of the above components included in the communication terminal 22 has a similar function as the similarly-named component in the first embodiment described with reference to FIG. 4. Note that in this system, since the attributes of each user are managed in the attribute management server 41, the situation information generation unit 2211 may acquire user attributes from the attribute management server 41 via the network I/F 2221. Also, the communication control unit 2212 controls the transmission of situation information generated by the situation information generation unit 2211 to the matching server 31 by the network I/F 2221 in association with the ID of the user. Also, in the case in a situation is determined by the matching server 31 to be handleable and a notification of the start of a kindness session is received, the presentation control unit 2213 issues an act-of-kindness recommendation notification to the user by causing the presentation device 11 to vibrate or the like. Alternatively, in the case in which a user capable of handling a situation is found by the matching server 31 and a notification of the start of a kindness session is received, the presentation control unit 2213 notifies the user that a kind person is around one by causing the presentation device 11 to vibrate or the like.

2-2-2. Configuration of Matching Server 31

Figure 9:
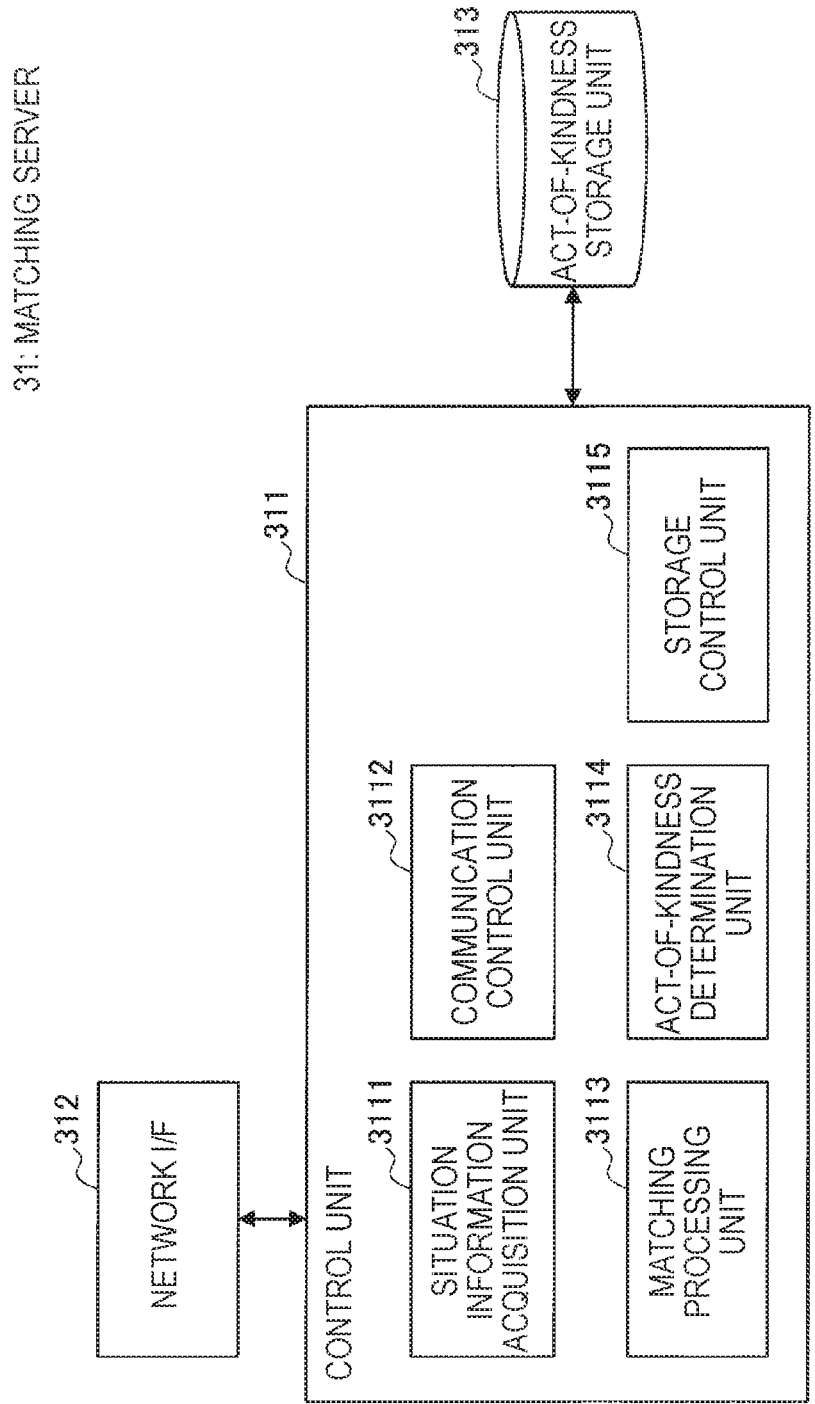
FIG. 9 is a block diagram illustrating an exemplary configuration of a matching server according to the present embodiment.

FIG. 9 is a block diagram illustrating an exemplary configuration of a matching server 31 according to the second embodiment. As illustrated in FIG. 9, the matching server 31 includes a control unit 311, a network I/F 312, and an act-of-kindness storage unit 313. The control unit 311 functions as a situation information acquisition unit 3111, a communication control unit 3112, a matching processing unit 3113, an act-of-kindness determination unit 3114, and a storage control unit 3115.

The situation information acquisition unit 3111 receives and acquires situation information from the communication terminal 22 by the network I/F 312 via the network 50.

The communication control unit 3112 controls the notification of the start of a kindness session from the network I/F 312 to a user as a result of matching by the matching processing unit 3113, for example, or in other words, a user included in a list of users determined to be capable of handling a situation indicated by situation information.

The matching processing unit 3113 determines whether or not a second user is capable of handling the situation of the first user, on the basis of situation information (context) of the first user, attributes of a second user present around one, and a current situation (action) of that second user. The specific handleability determination process is similar to that of the handleability determination unit 2113 according to the first embodiment.

Also, the matching processing unit 3113 may make a list of users capable of handling the situation indicated by the situation information of the first user, and in the case in which multiple users capable of handling the situation are present, select a user to notify of the start of a kindness session in accordance with an order of priority, and update the list. The order of priority is not particularly limited, but may prioritize a user having a small number of acts of kindness, for example. Additionally, the matching processing unit 3113 may also assign a kindness session ID to the generated list.

The act-of-kindness determination unit 3114 determines whether or not an act of kindness has been conducted, on the basis of a change in the situation (action) of the first user, and a change in the situation of a user notified of the start of a kindness session.

In the case in which the act-of-kindness determination unit 3114 determines that an act of kindness has been performed, the storage control unit 3115 controls the storage of information related to the act of kindness in the act-of-kindness storage unit 313. At this point, the act-of-kindness storage unit 313 stores information such as the time, the place, the ID of the person performing the act of kindness, the ID of the person receiving the act of kindness, the content of the act of kindness, and a kindness session ID in association with each other as the information related to the act of kindness.

The network I/F 312 connects to and transmits or receives information with an external device over the network 50. For example, the network I/F 312 connects to the attribute management server 41 and the communication terminal 22 via the network 50, and transmits or receives information.

2-2-3. Operating Process

Next, an operating process according to the present embodiment will be described with reference to FIGS. 10 to 13. FIGS. 10 to 13 are sequence diagrams illustrating an operating process of an act-of-kindness support system according to the second embodiment.

Figure 10:
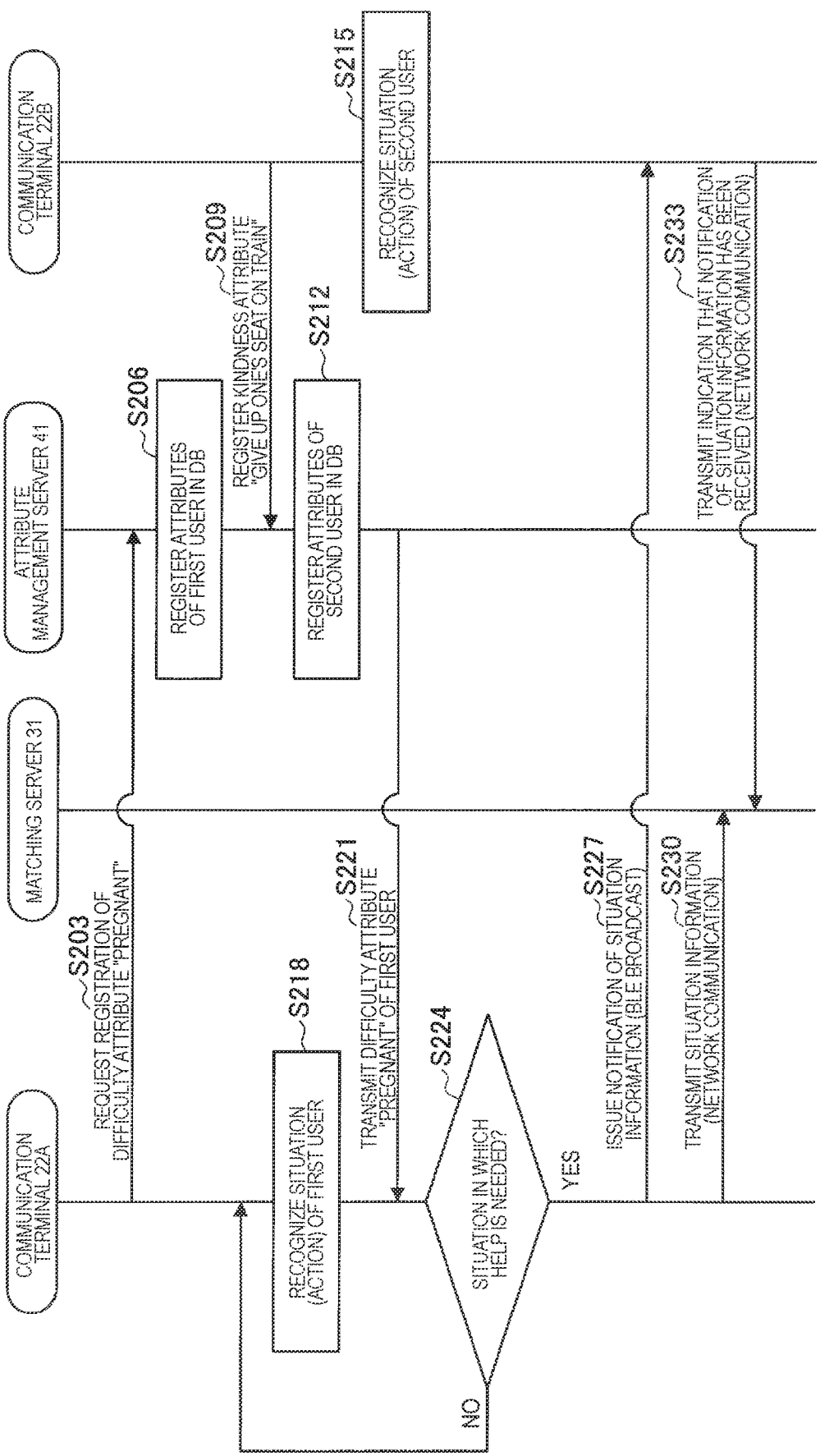
FIG. 10 is a sequence diagram illustrating an operating process of an act-of-kindness support system according to the present embodiment.

As illustrated in FIG. 10, first, the communication terminal 22A requests the attribute management server 41 to register a difficulty attribute "pregnant" of the first user, in accordance with an operation by the first user (step S203), and the attribute management server 41 registers the attribute of the first user in a DB (step S206).

Meanwhile, the communication terminal 22B requests the attribute management server 41 to register a kindness attribute "give up one's seat on a train" of the second user, in accordance with an operation by the second user (step S209), and the attribute management server 41 registers the attribute of the second user in a DB (step S212).

Subsequently, in the communication terminal 22A, the situation acquisition unit 2210 conducts situation (action) recognition of the first user (step S218). Specifically, the situation acquisition unit 2210 conducts user action recognition on the basis of sensing data such as acceleration data sensed by the acceleration sensor 114 of the presentation device 11A.

Next, the situation information generation unit 2211 of the communication terminal 22A acquires the difficulty attribute of the first user from the attribute management server 41 (step S221), and on the basis of the difficulty attribute of the first user and the current situation (difficulty) of the first user), determines whether or not there is a situation in which help is needed (step S224).

Subsequently, in the case of determining that there is a situation in which help is needed (step S224/Yes), the communication terminal 22A notifies the communication terminal 22B existing around one of the situation information (for example, context such as "wanting someone to give up their seat") generated by the situation information generation unit 2211 (step S227). At this point, for example, the communication terminal 22A may also broadcast the situation information to one or more surrounding communication terminals by using BLE, which is one example of the short-range communication unit 2222.

Also, the communication terminal 22A transmits the situation information generated by the situation information generation unit 2211, in association with the ID of the first user, from the network I/F 2221 to the matching server 31 via the network 50 (step S230).

Next, the communication terminal 22B transmits a signal indicating that the notification of situation information has been received, in association with the ID of the second user, from the network I/F 2221 to the matching server 31 via the network 50 (step S233).

Figure 11:
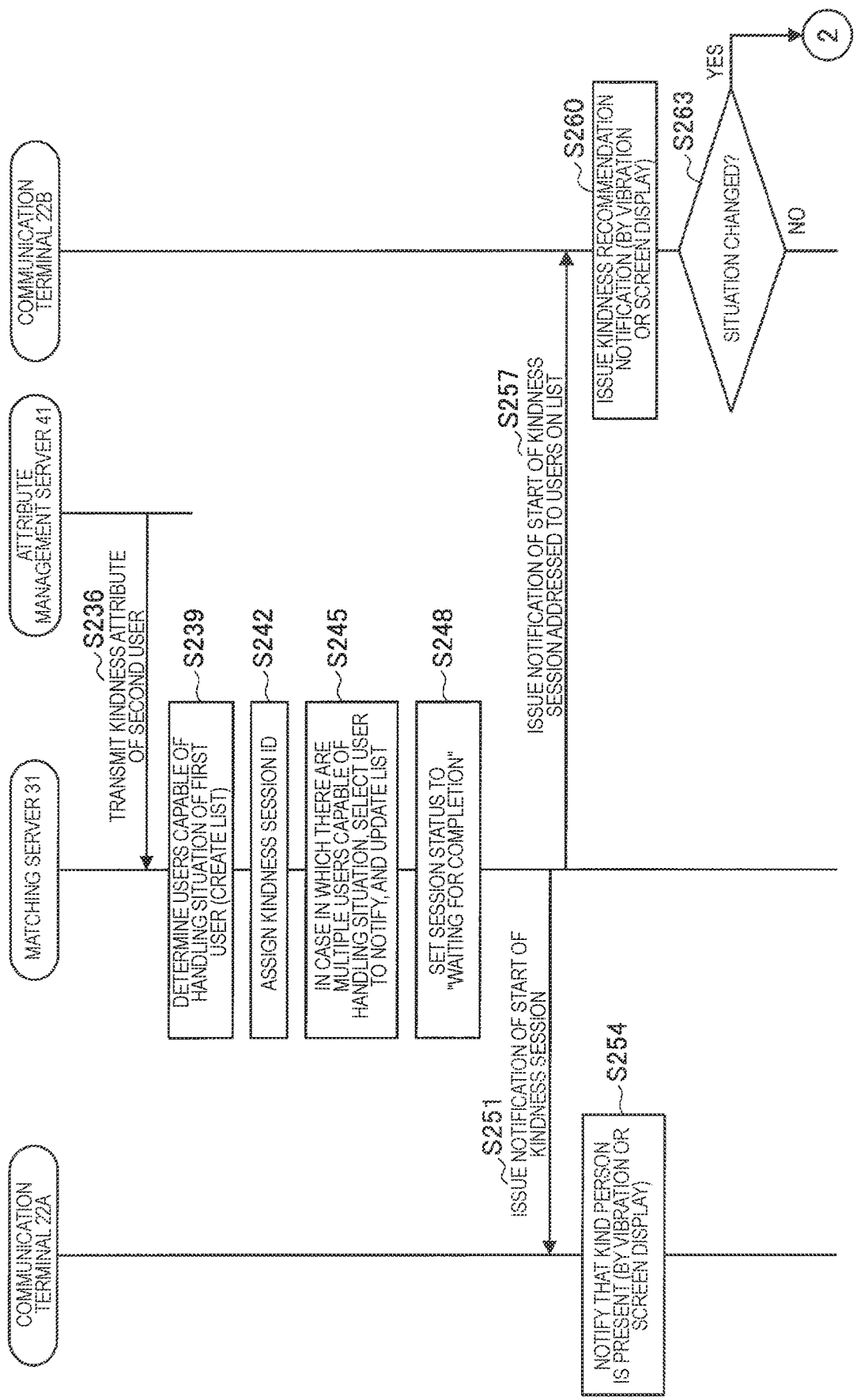
FIG. 11 is a sequence diagram illustrating an operating process of an act-of-kindness support system according to the present embodiment.
Figure 12:
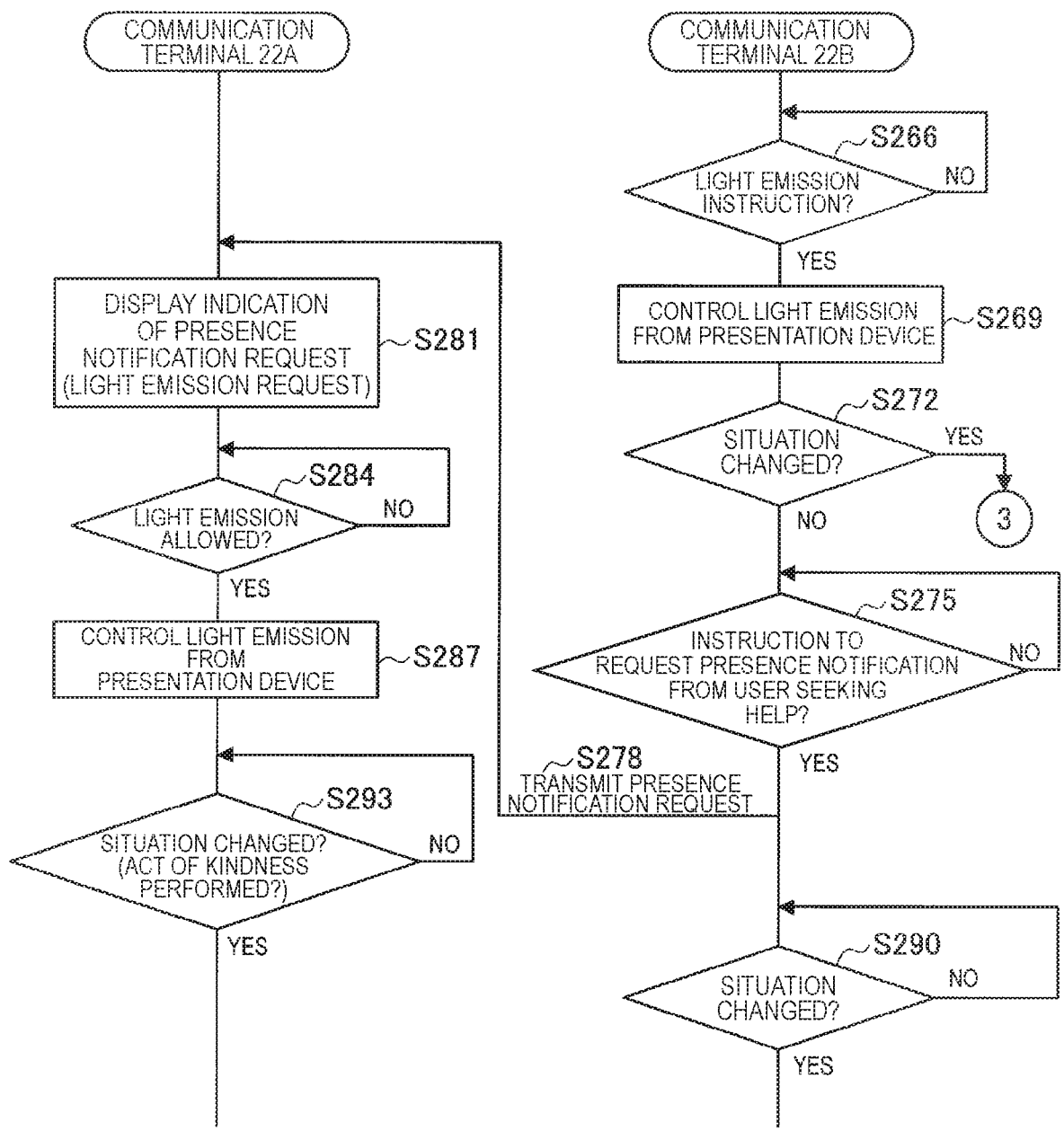
FIG. 12 is a sequence diagram illustrating an operating process of an act-of-kindness support system according to the present embodiment.

Subsequently, the matching server 31 uses the ID of the second user that transmitted the above signal indicating that the notification of situation information has been received, and acquires the kindness attribute of that second user from the attribute management server 41 (step S236 in FIG. 11).

Next, the matching processing unit 3113 of the matching server 31 references the kindness attribute of the second user acquired in the above step S236 to determine and make a list of users capable of handling the situation (context) indicated by the situation information of the first user received from the communication terminal 22A in the above step S230 (step S239). At this point, in the case of also receiving the situation (action) of the second user in addition to the indication of reception of the notification of situation information from the communication terminal 22B in the above S233, the matching processing unit 3113 jointly references the kindness attribute and the situation (action) of the second user to determine whether or not the situation of the first user is handleable. Alternatively, in the case in which an action management server (not illustrated) exists on the network, and a daily action history of each user (such as time, position information, and means of transportation information) is stored continuously, the matching server 31 may also acquire the situation (action) of the second user from such an action management server. Note that after receiving situation information from the communication terminal 22A in the above S230, the matching server 31 may conduct the processing in S236 and S239 above with respect to one or more other communication terminals that have transmitted an indication of reception of the situation information from that communication terminal 22A within a fixed time, for example.

Subsequently, in the case in which a user capable of handling the situation is present, the matching processing unit 3113 associates a kindness session ID to the generated list (step S242).

Next, in the case in which multiple users capable of handling the situation are present, the matching processing unit 3113 selects a user to notify of a kindness recommendation, and updates the list (step S245). The user selection method is not particularly limited, and the matching processing unit 3113 may select the user to notify of a kindness recommendation by referencing the kindness action history of the target user (stored in the act-of-kindness storage unit 313) so that kindness opportunities are not biased towards specific users. Additionally, the matching processing unit 3113 may also not select a specific user, and instead notify all users capable of handling the situation.

Subsequently, the matching processing unit 3113 sets a status corresponding to the kindness session ID to "waiting for completion" (step S248).

Next, the communication control unit 3112 of the matching server 31 notifies the communication terminal 22A and each user included in the generated list (herein, the communication terminal 22B) of the start of a kindness session (steps S251, S257).

Next, the communication terminal 22A notifies the first user, with vibration of the presentation device 11A or a screen display from the display unit 226 of the communication terminal 22A, of the presence of a kind person around one (step S254). With this arrangement, the first user is able to look around or the like, and accept the kindness of the second user more easily.

In addition, the communication terminal 22B controls the issuing of a kindness recommendation notification to the second user, with vibration of the presentation device 11B or a screen display from the display unit 226 of the communication terminal 22B (step S260). With this arrangement, the second user is able to recognize that a person around one wants someone to give up their seat, look around and visually find the target user, and give up one's seat.

Subsequently, the communication terminal 21B uses the situation acquisition unit 2210 to determine whether or not the situation (action) of the second user has changed (step S263).

Next, in the case in which the situation has not changed (step S263/No), in accordance with a light emission instruction from the second user (step S266/Yes), the communication terminal 22B causes the presentation device 11B to emit light (step S269). With this arrangement, the second user is able to indicate one's own presence to the other person (herein, the first user).

In the case in which the users still do not notice each other and the situation of the second user does not change (step S272/No)), the second user is able to request a presence notification from the user seeking help (S275).

Subsequently, in the case in which there is an instruction for a presence notification request from the second user (step S275/Yes), the communication control unit 2212 of the communication terminal 22B controls the transmission of a presence notification request to the communication terminal 22A via the short-range communication unit 2222 (step S278).

Next, the presentation control unit 2213 of the communication terminal 22A presents a display on the display unit 226 or the like to notify the first user of a presence notification request (herein, a light emission request) from a surrounding communication terminal 22 (step S281). For example, the presentation control unit 2213 displays on the display unit 216 a screen which indicates a light emission request for an act of kindness from a surrounding communication terminal 22, and which includes light emission OK and No buttons.

Subsequently, in the case in which light emission is allowed by the first user (step S284/Yes), the presentation control unit 2213 controls, via the short-range communication unit 2222, the emission of light from the presentation device 11A worn by the first user (step S287). Note that herein, light emission control is conducted in the case of presenting a presence notification request to the first user and being allowed, but the present embodiment is not limited thereto, and light emission OK/No when there is a light emission request may also be set by the first user in advance, for example.

In this way, by ultimately also causing the presentation device 11A of the first user to emit light, the second user has a higher probability of finding the first user, and an act of kindness can be supported.

Next, the case in which the situations (actions) of the first user and the second change (step S263/Yes, S272/Yes, S284/Yes, S290/Yes) will be described with reference to the sequence diagram in FIG. 13.

Figure 13:
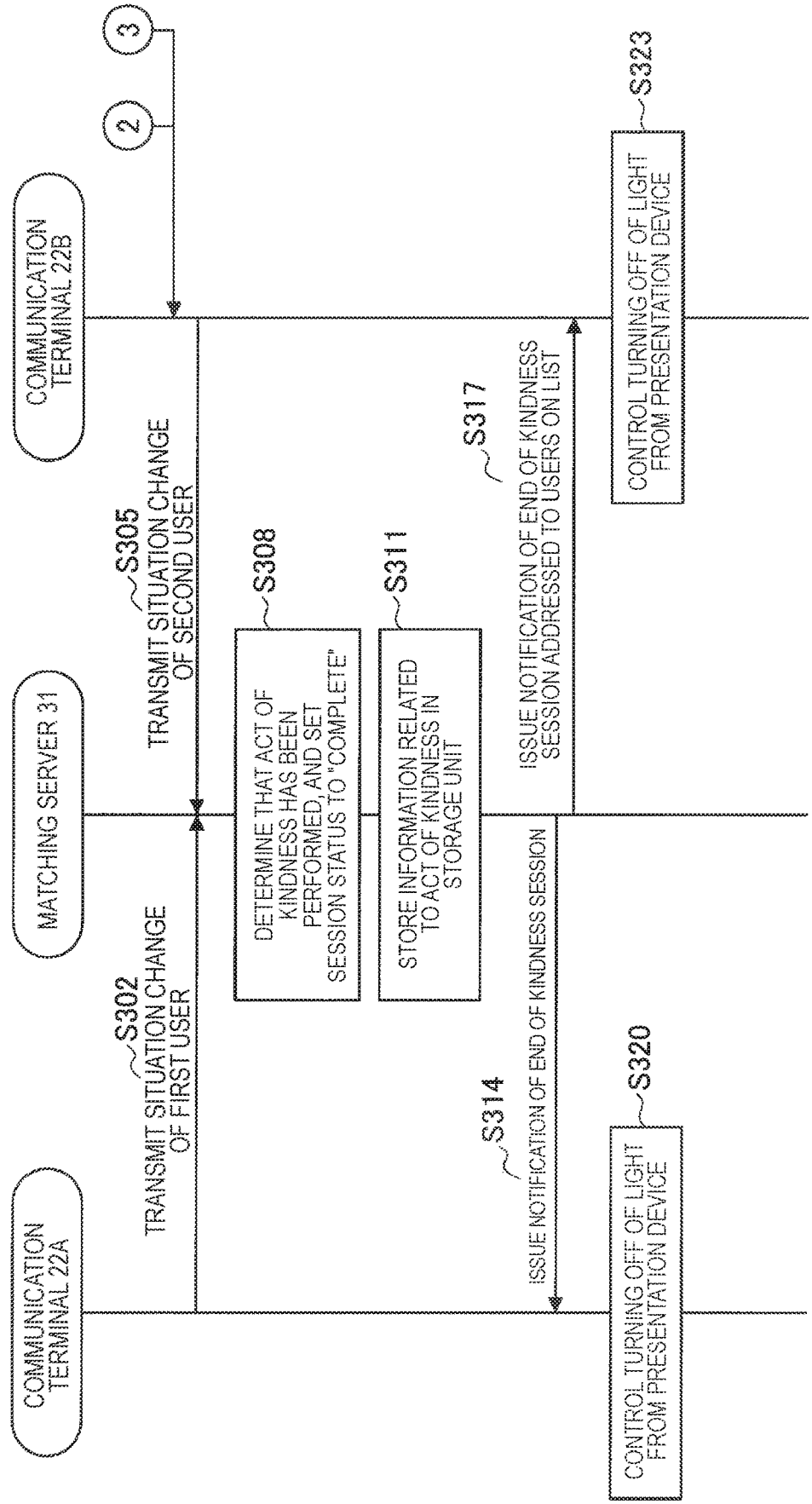
FIG. 13 is a sequence diagram illustrating an operating process of an act-of-kindness support system according to the present embodiment.

As illustrated in FIG. 13, in the case in which the situation of the first user acquired by the situation acquisition unit 2210 changes (for example, in the case of sitting down from a standing state), the communication terminal 22A transmits the content of the situation change to the matching server 31 (step S302).

Meanwhile, in the case in which the situation of the second user acquired by the situation acquisition unit 2210 changes (for example, in the case of standing up from a sitting state), the communication terminal 22B also transmits the content of the situation change to the matching server 31 (step S305).

Subsequently, the act-of-kindness determination unit 3114 of the matching server 31 determines whether or not an act of kindness has been performed on the basis of the situation change of the first user and the situation change of the second user, and in the case of determining that an act of kindness has been performed, sets the status of the relevant kindness session to "Complete" (step S308). For example, in a kindness session of giving up one's seat on a train, in the case in which the situation of the first user changes from a standing state to a sitting situation while the situation of a second user present around one changes from a sitting state to a standing situation, the act-of-kindness determination unit 3114 can determine that the second user has performed an act of kindness of giving up one's seat to the first user. Also, the act-of-kindness determination unit 3114 may also determine whether or not an act of kindness has been performed by additionally determining that both situation changes have occurred within a certain amount of time, and both are within a certain distance.

Next, the storage control unit 3115 controls the storage of information related to the act of kindness, namely the time, the place, the ID of the person performing the act of kindness, the ID of the person receiving the act of kindness, the content, and the kindness session ID, in association with each other in a storage unit (step S311).

Subsequently, the communication control unit 3112 transmits a kindness session end notification addressed to the communication terminal 22A and each user included in the list (herein, the communication terminal 22B) (steps S314, 317).

Subsequently, the communication terminal 22A and the communication terminal 22B control the turning off of light from the presentation devices 11A and 11B, respectively (S320, S323). Note that in the case in which multiple users are included in the list, in the communication terminal 22 of a user other than the user who performed the act of kindness, a notification that an act of kindness has been performed by another user and the kindness session has ended may be displayed on the display unit 226 or the like.

2-2-4. Effects

The above thus specifically describes an act-of-kindness support system according to the second embodiment. In the present embodiment, by matching a person needing help and a person wanting to perform an act of kindness to each other on the server side, it becomes possible to issue a kindness recommendation notification preferentially to a specific user in the case in which multiple persons wanting to perform an act of kindness are present, for example.

Also, in the present embodiment, by taking a configuration in which the matching process and the act-of-kindness determination process are provided on the server side, it becomes possible to reduce the processing load on the communication terminal 22 side.

Also, in the present embodiment, by taking a configuration in which the act-of-kindness storage unit is provided on the server side, integrated management of acts of kindness by multiple users becomes possible.

3. APPLIED EXAMPLES

3-1. First Applied Example

The respective embodiments described above all describe an act-of-kindness support system envisioning a situation on a train, but the above embodiments are one example, and an act-of-kindness support system according to the present disclosure obviously is also applicable to other situations. Hereinafter, applied examples of an act-of-kindness system according to the present disclosure will be described.

The first applied example describes an act-of-kindness support system envisioning a situation in which a child having an allergy or a child with a dislike of a particular food/thing is present at a school or a friend's home. For example, when a child visits one's home to play, one must not mistakenly give a child having an allergy some food containing the allergen, but it is difficult to grasp all of a child's allergies in advance, and even if one asks the child him- or herself, the child may be unable to answer accurately in some cases. Consequently, the present applied example enables an adult to grasp that a child having an allergy is present nearby, and to not serve food containing the allergen, thereby supporting unobtrusive actions of avoiding danger (an example of an act of kindness).

3-1-1. Overview

Figure 14:
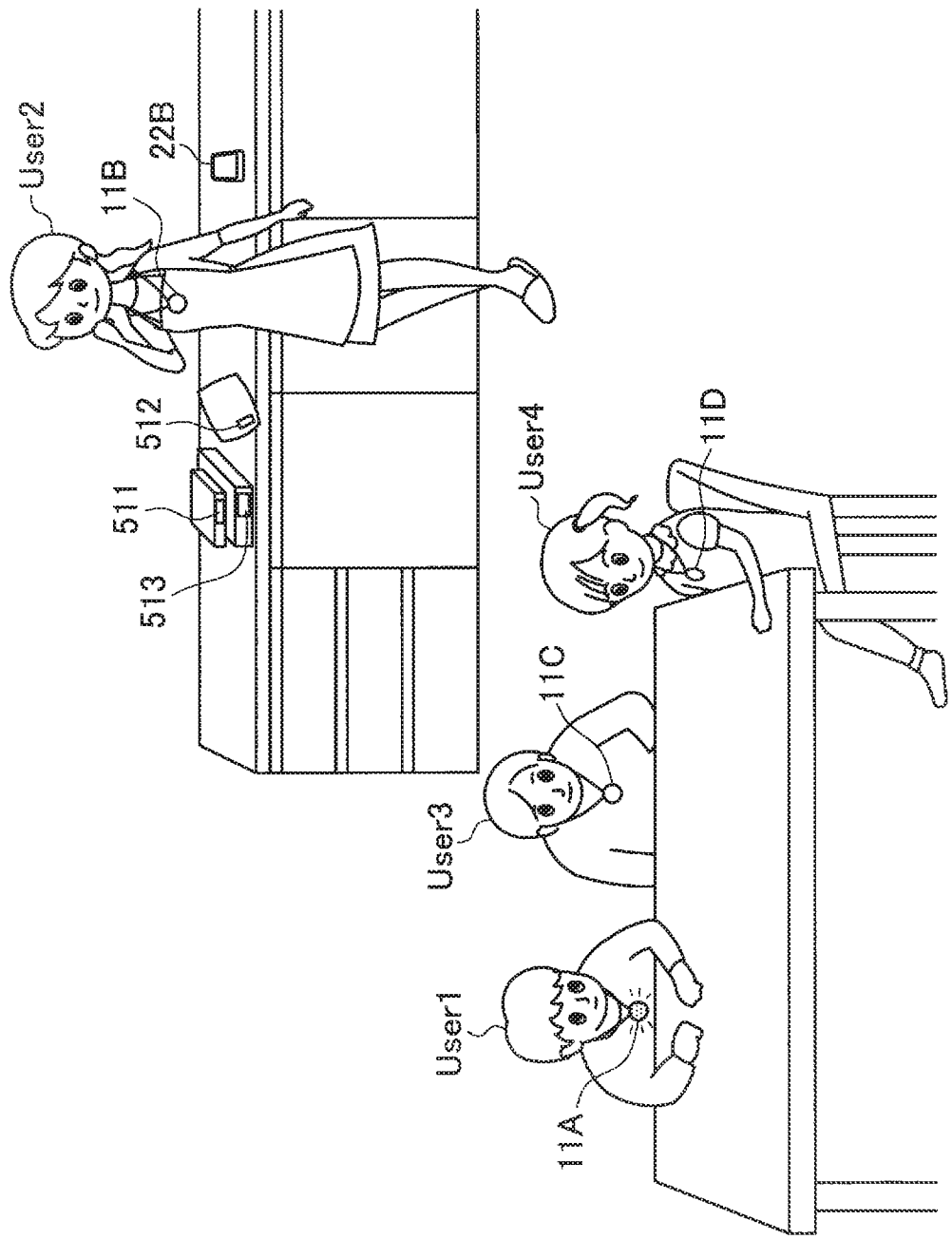
FIG. 14 is a diagram explaining an example of a scene where an act-of-kindness support system according to a first applied example is applied.

FIG. 14 is a diagram explaining an example of a scene where an act-of-kindness support system according to the first applied example is applied. The illustrated example envisions a situation in which friends (User1 and User4) come to the home of a child (User3) to play, and the parent (User2) of the child (User3) provides food to the children. As described above, in such a case, if a child having an allergy is among the children who have come to play, the parent tries not to provide food containing the target allergens, but it is difficult to grasp which child has what allergy entirely in advance. Accordingly, in the present applied example, on the basis of object attributes included in ID tags 511, 512, and 513 affixed to food boxes and bags, and preregistered user attributes (specifically, difficulty attributes related to allergies), it is determined whether or not there is a situation in which help is needed (that is, whether or not a food that cannot be eaten is nearby). If there is a situation in which help is needed, a help signal is broadcast to surroundings from a communication terminal of the child (User1). In the present applied example, the registration of kindness attributes on the parent (User2) side is unnecessary, and it is sufficient to be able to receive a help signal from a surrounding communication terminal. The communication terminal 22B of the parent (User2) receiving the help signal displays the content, warning the parent (User2) that a person having an allergy exists around one, and that it is dangerous to provide that person with food containing the target allergen. With this arrangement, the parent is able to handle the situation by not providing food containing the target allergen. Note that in the case of wanting to clearly know which child needs help (which child has the allergy), it is also possible to cause the presentation device 11 being worn by the child to emit light.

Additionally, the configuration of the act-of-kindness support system according to the first applied example may be either the act-of-kindness support system 101 according to the first embodiment illustrated in FIG. 2, or the act-of-kindness support system 102 according to the second embodiment illustrated in FIG. 7. Herein, as an example, a configuration similar to the act-of-kindness support system 102 according to the second embodiment, namely a configuration including the communication terminal 22A of a first user (herein, the user having an allergy), the communication terminal 22B of a second user (herein, the parent providing food), and the matching server 31, is used. The communication terminals 22A and 22B and the matching server 31 are connected via a network 50 and able to transmit or receive data. Also, an attribute management server 41 is connected to the network 50, and the matching server 31 may acquire attributes of a target user from the attribute management server 41. The attribute management server 41 according to the present applied example also manages object attributes in addition to user attributes. Object attributes are associated with an ID assigned to types of objects (for example, each product), for example. In the case of food, for example, object attributes indicate information related to the ingredients, such as if allergen information (such as eggs, milk, wheat, buckwheat, peanuts, shrimp, or crab) is included, if substances restricted for vegetarian or religious reasons (such as beef, pork, fish, eggs, or alcohol) are included, or if alcohol is included. In addition, information related to production methods, such as whether or not a food is genetically modified.

Also, the communication terminal 22 connects to the presentation device 11 worn by a user, and controls light emission and vibration of the presentation device 11.

Also, the communication terminal 22 may acquire the ID of a food from an ID tag affixed to the food, and on the basis of the ID, acquire food attributes from the attribute management server 41 (alternatively, the communication terminal 22 may acquire food attributes from the ID tag of the food). The ID tag may be realized by a short-range communication device such as a near field communication (NFC) sticker, or a BLE device, for example. Herein, a BLE tag is used as an example.

3-1-2. Operating Process

Figure 15:
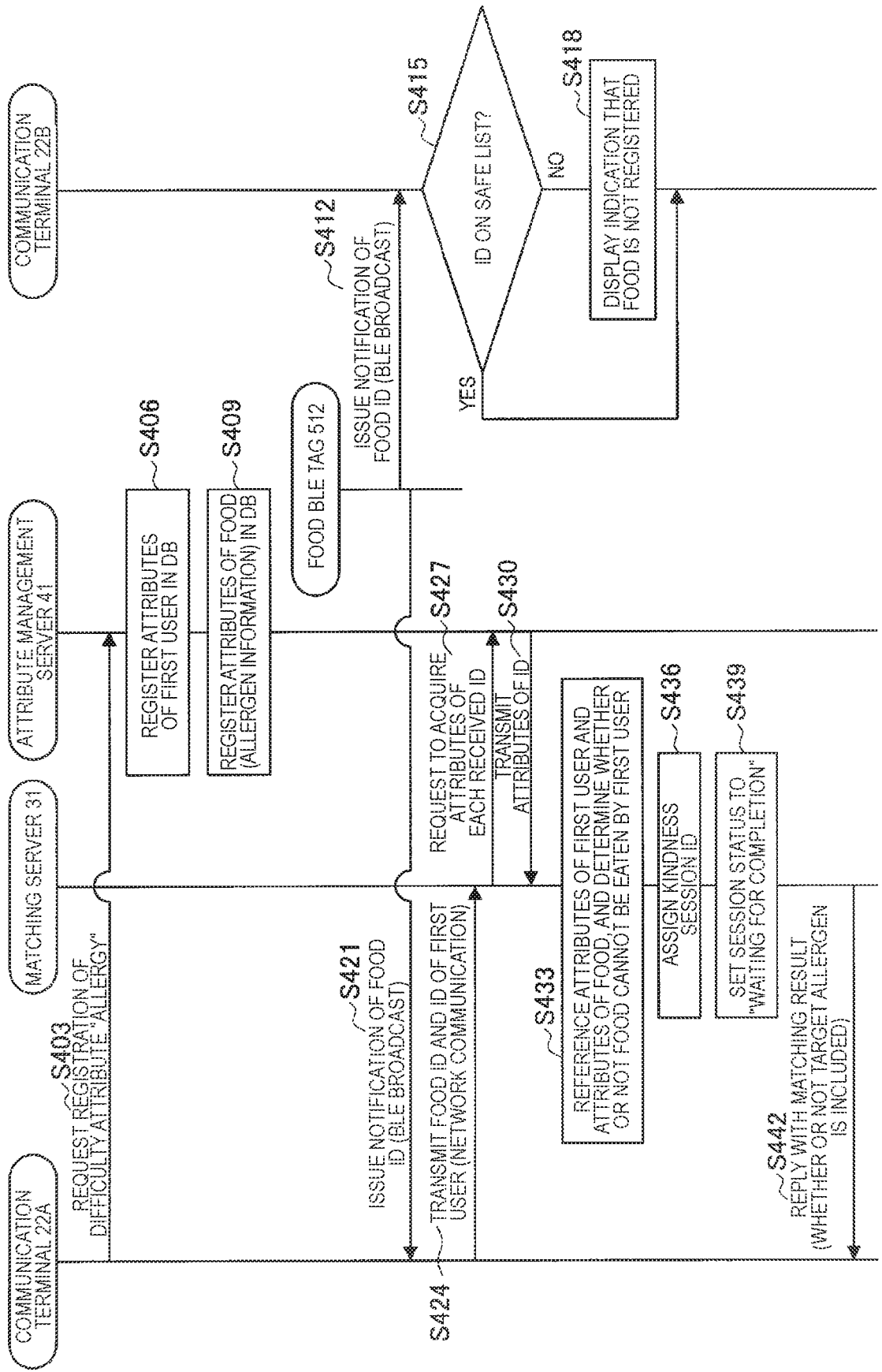
FIG. 15 is a sequence diagram illustrating an operating process of an act-of-kindness support system according to the first applied example.
Figure 16:
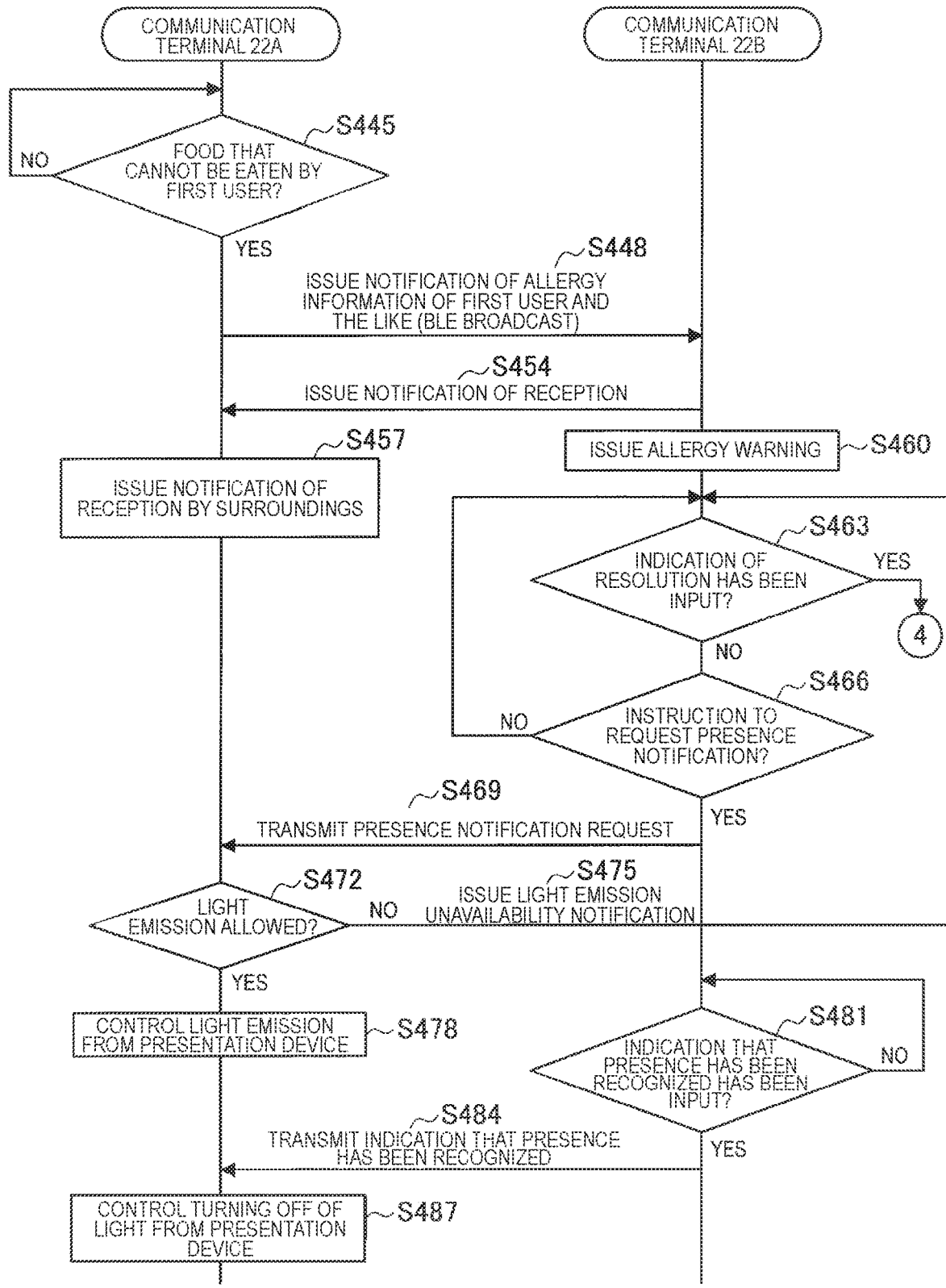
FIG. 16 is a sequence diagram illustrating an operating process of an act-of-kindness support system according to the first applied example.
Figure 17:
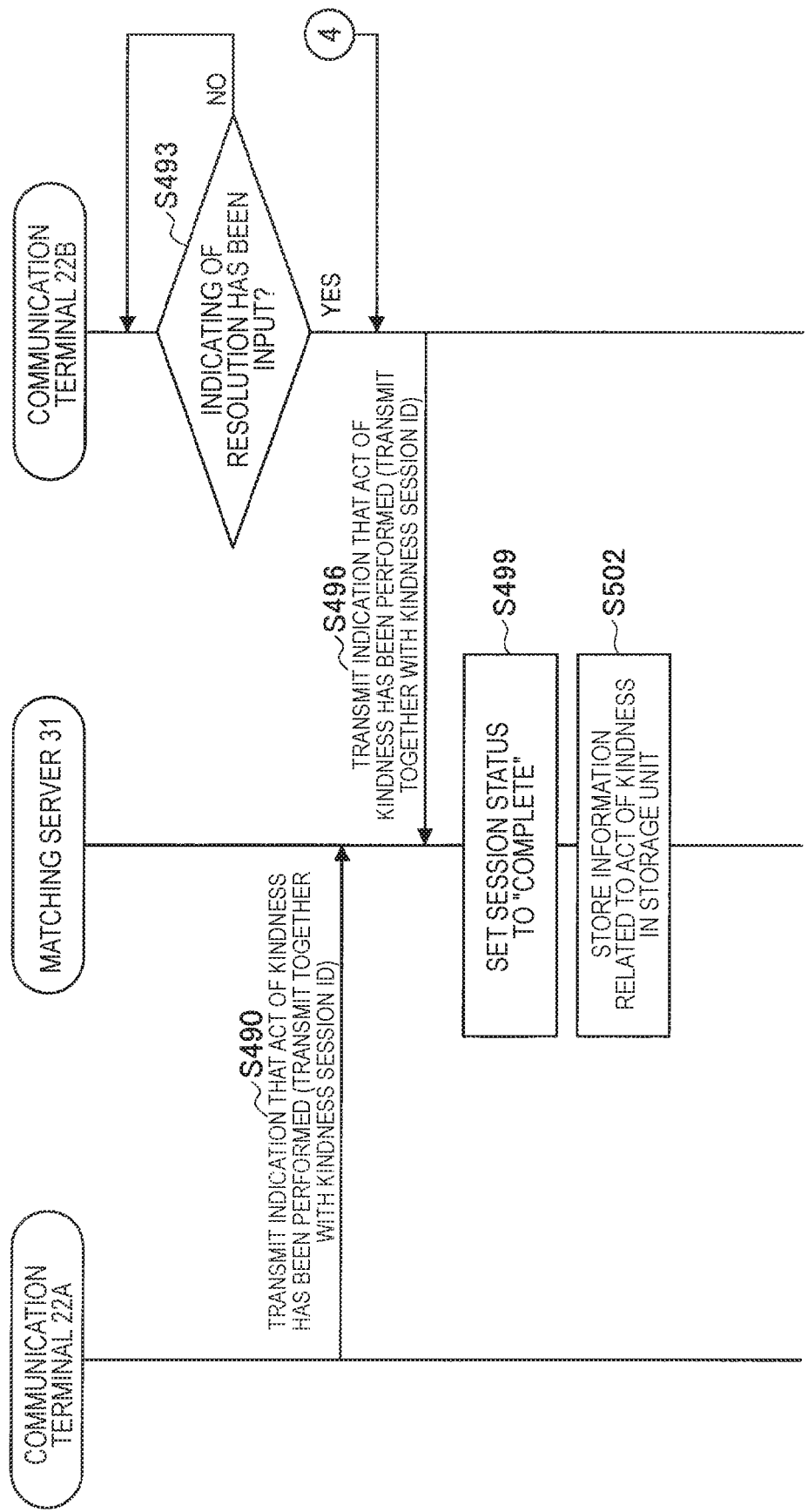
FIG. 17 is a sequence diagram illustrating an operating process of an act-of-kindness support system according to the first applied example.

Next, an operating process according to the present applied example will be described with reference to FIGS. 15 to 17. FIGS. 15 to 17 are sequence diagrams illustrating an operating process of an act-of-kindness support system according to the first applied example.

As illustrated in FIG. 15, first, the communication terminal 22A requests the attribute management server 41 to register a difficulty attribute of the first user (having an allergy with respect to a specific food), in accordance with a user operation (step S403), and the attribute management server 41 registers the attribute of the first user in a DB (step S406). Note that the registration of a difficulty attribute may be conducted not by the child him- or herself, but instead by a parent, or by a doctor on the basis of a diagnosis.

In addition, the attribute management server 41 registers food attributes (ingredient information such as allergens) in accordance with an instruction from the food producer or a third party (step S409).

Next, a BLE tag 512 affixed to the food periodically uses a BLE broadcast to notify a surrounding communication terminal of its own ID (hereinafter designated the food ID) (steps S412, S421). Note that the BLE tag may also be presupposed to be provided only on foods that include substances requiring attention, such as allergens. With this arrangement, the food to which the BLE tag 512 is affixed can make known information such as its own allergens to a communication terminal existing nearby.

Next, the control unit 221 of the communication terminal 22B determines whether or not the acquired food ID is on a preset safe list (step S415). The safe list is a registration of allergens that pose no health problems even when presented to one's family at one's home, registered in the communication terminal 22B in advance by the second user. In the case in which the food ID is not on the safe list (step S415/No), the communication terminal 22B notifies the second user by displaying that the food is unregistered. In the case in which the food ID is on the safe list (step S415/Yes), no notification is issued.

In addition, the communication terminal 22A transmits food IDs received from the BLE tags of foods existing nearby to the matching server 31 in association with the ID of the first user as situation information about the first user (that is, a situation in which the foods indicated by the relevant food IDs exist near the first user) (step S424).

Next, the matching server 31 issues to the attribute management server 41 a request to acquire the attributes of each received ID (step S427).

Subsequently, the attribute management server 41 transmits to the matching server 31 the attributes of each requested ID (step S430).

Next, the matching processing unit 3113 of the matching server 31 references the attributes of the first user and the food attributes, and determines whether or not there is a food that the first user cannot eat (specifically, whether or not a target food includes an allergen indicated by the difficulty attribute of the first user) (step S433).

Subsequently, in the case of determining that there is a food that the first user cannot eat (that is, a state in which the first user needs help), the matching processing unit 3113 assigns a kindness session ID (step S436). The kindness session ID is associated with information related to an act of kindness, such as the ID of the first user, the food ID, the time, the place, and the kindness content (not providing a food that includes an allergen), for example.

Next, the matching processing unit 3113 sets the session status corresponding to the assigned kindness session ID to "waiting for completion" (step S439).

Subsequently, the communication control unit 3112 of the matching server 31 replies to the communication terminal 22A with whether or not there is a food containing a target allergen as a matching result (step S442). In the case in which the kindness session ID has been assigned, the kindness session ID is also included in the reply. Note that although the sequence illustrated in FIG. 15 indicates only a process with respect to a food ID from the BLE tag 512, this is one example, and food IDs may be broadcast to surroundings similarly from the other BLE tags 511 and 513 illustrated in FIG. 14, and a similar process may be conducted.

Next, as illustrated in FIG. 16, in the case in which the matching result indicates that there is a food that the first user cannot eat (in other words, there is a food containing a target allergen) (step S445/Yes), the communication terminal 22A notifies surroundings that a food which cannot be eaten is close by (that is, there is a situation in which help is needed: a help signal) (step S448). Specifically, the communication control unit 2212 of the communication terminal 22A transmits the allergy information of the first user, the food ID, and the kindness session ID to communication terminals existing around one by a BLE broadcast.

On the other hand, in the case of a food that the first user can eat (step S445/No), the communication terminal 22A does not issue any notification.

Subsequently, the communication terminal 22B replies to the communication terminal 22A that the BLE notification has been received (step S454).

Next, the communication terminal 22A uses vibration, a screen display, sound, or the like to notify the first user that the BLE notification has been received by one or more surrounding communication terminals 22 (step S457).

Also, the communication terminal 22B issues an allergy warning in accordance with the BLE notification from the communication terminal 22A (step S460). Specifically, for example, the presentation control unit 2213 of the communication terminal 22B issues an allergy warning by displaying on the display unit 226 an indication that a person in danger of being provided a food that cannot be eaten is present around one, together with information about the target allergen, the food ID, and a product name based on the food ID. In addition, the allergy warning is not limited to a display-based notification, and may also be issued by a notification using vibration, light, sound, or the like. On the basis of the displayed food ID or product name based on the food ID, as well as the information about the target allergen, the second user is able to confirm and not provide the target food.

Subsequently, the control unit 221 of the communication terminal 22B determines whether or not a resolution of the matter warned about has been input (step S463). In the case in which the problematic food can be specified in accordance with the allergy warning of the communication terminal 22B, the second user can resolve the matter warned about by not providing the specified food to a surrounding person. In this case, the second user can tap a Resolve button displayed on the screen of the display unit 226, for example, and input that the matter warned about has been resolved. On the other hand, in the case in which multiple persons are present around one, the second user is not necessarily required not to provide the problematic food to everyone, and if the person with the allergy can be specified, it is also possible to resolve the matter by not providing the problematic food only to the relevant person. In the case of wanting to specify the person with the allergy, the second user taps an "external presence notification request button" displayed on the screen of the communication terminal 22B or performs a long-press on a specific button on the presentation device 11B, for example, and thereby inputs an instruction to request a presence notification to the outside.

Next, in the case in which there is an instruction for a presence notification request for specifying the person with the allergy (step S466/Yes), the communication control unit 2212 of the communication terminal 22B controls the transmission of a presence notification request to the communication terminal 22A via the short-range communication unit 2222 (step S469).

Next, in the case in which light emission is allowed (step S472/Yes), the presentation control unit 2213 of the communication terminal 22A controls, via the short-range communication unit 2222, light emission from the presentation device 11A worn by the first user (step S478). The allowing of light emission may be allowed by the first user (child) or a parent of the first user in advance, or approval may be obtained from the first user every time (for example, a light emission allow/deny button is displayed on the display unit 226). In this way, by causing the presentation device 11A of the first user to emit light, the second user is able to specify the person with the allergy, and perform an act of kindness of not providing the problematic food to only the relevant person.

On the other hand, in the case in which light emission is not allowed (step S427/No), the communication terminal 22A issues a light emission unavailability notification to the communication terminal 22B (step S475). The communication terminal 22B receiving the light emission unavailability notification can display on the display unit 226 an indication that specification of the person with the allergy is unavailable, and encourage the second user not to provide the problematic food to everyone.

Subsequently, in the case in which the presentation device 11A emits light and the person with the allergy can be specified, the second user taps a presence recognition button displayed on the display unit 226 of the communication terminal 22B, for example, and inputs that the presence has been recognized (step S481).

Next, in the case in which recognition of the presence is input (step S481/Yes), the communication control unit 2212 of the communication terminal 22B notifies the communication terminal 22A that the presence has been recognized (step S484).

Subsequently, the presentation control unit 2213 of the communication terminal 22A, having confirmed that one's own presence has been recognized, controls the turning off of light from the presentation device 11A (step S487).

Next, the case in which the matter warned about (herein, the presence of a person in danger of eating a food containing a corresponding allergen) is resolved by the second user (that is, the case in which an act of kindness is performed) will be described with reference to the sequence diagram in FIG. 17.

As illustrated in FIG. 17, first, the communication terminal 22A transmits an indication that an act of kindness has been performed, together with the kindness session ID, to the matching server 31 from the network I/F 2221 (step S490). The notification that an act of kindness has been performed may be issued when triggered by the reception of the presence recognition notification in the above step S484, or when triggered by the second user telling the first user directly that his or her presence has been recognized, and the first user tapping an act-of-kindness end button or a problem resolution button displayed on the display unit 226 of the communication terminal 22A. Note that in the case in which the person with the allergy is not specified, such a notification is not issued from the communication terminal 22A to the matching server 31.

Next, in the communication terminal 22B, in the case in which an indication that the matter warned about has been resolved (that is, an indication that an act of kindness has been performed) is input by the second user (step S463/Yes, 493/Yes), the communication control unit 2212 transmits an indication that an act of kindness has been performed, together with the kindness session ID, to the matching server 31 from the network I/F 2221 (step S496).

Subsequently, in the case of receiving an indication that an act of kindness has been performed from the communication terminals 22A and 22B, the act-of-kindness determination unit 3114 of the matching server 31 sets the status of the relevant kindness session to "Complete" (step S499).

Additionally, the storage control unit 3115 controls the storage of information related to the act of kindness, namely the time, the place, the ID of the person performing the act of kindness, the ID of the person receiving the act of kindness, the content (including the food ID), and the kindness session ID, in association with each other in a storage unit (step S502).

The above thus describes an act-of-kindness support system related to the provision of food including an allergen according to the first applied example. Note that the applied example described above may also be conducted between the communication terminals 22A and 22B like the system configuration according to the first embodiment. In this case, the handleability determination, the act of kindness determination, and the control of the storage of information related to the act of kindness conducted on the matching server 31 side may be conducted on the communication terminal 22 side.

3-2. Second Applied Example

As explained in the embodiments and applied example described above, since information related to acts of kindness (situation handling history information) is accumulated in an act-of-kindness storage unit, an act-of-kindness support system is also capable of proposing actions to users on the basis of the accumulated act-of-kindness information, and promoting communication between persons who have performed acts of kindness. Information related to acts of kindness may be stored in the act-of-kindness storage unit 219 or 313, or may be accumulated as part of an action history in an action management server (not illustrated) on a network.

Figure 18:
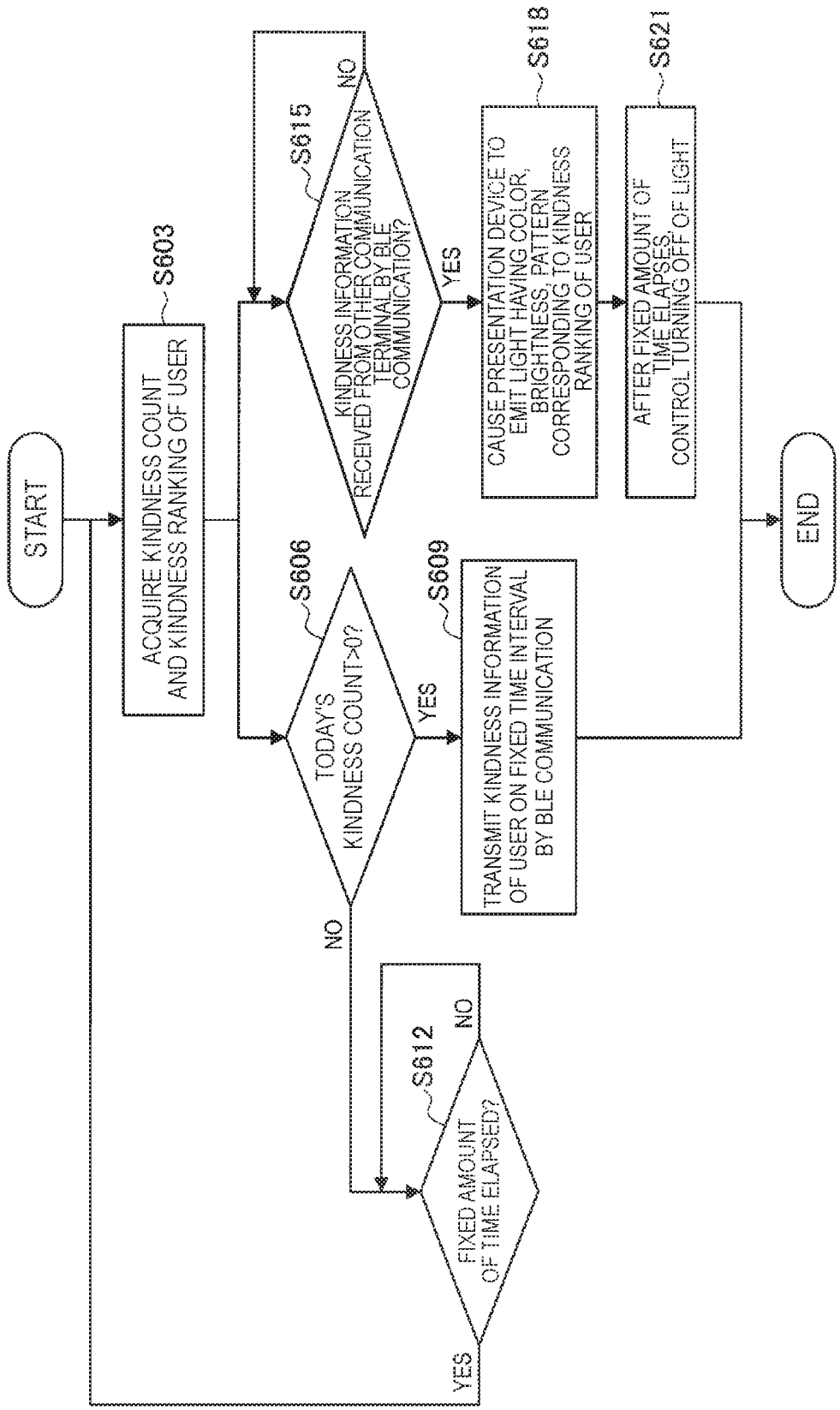
FIG. 18 is a flowchart illustrating an operating process according to a second applied example.

Herein, an example of the promotion of communication between persons who have performed acts of kindness will be described with reference to FIG. 18. FIG. 18 is a flowchart illustrating an operating process according to the second applied example. A case is supposed in which the process described below is conducted respectively by each communication terminal.

As illustrated in FIG. 18, first, the communication terminal 22 of a user acquires a kindness count and a kindness ranking of the user (step S603). The kindness count and kindness ranking of the user may be acquired from act-of-kindness information accumulated in the act-of-kindness storage unit 219 or 313, or in an action management server on a network.

Next, in the case in which the kindness count for today exceeds 0 times (step S606/Yes), the communication terminal 22 transmits kindness information about the user to surrounding communication terminals on a fixed time interval by BLE communication, for example.

On the other hand, in the case in which the kindness count for today is still 0 times (step S606/No), the communication terminal 22 repeats the above steps S603 and S606 every time a fixed amount of time elapses (step S612).

Also, in the case of receiving kindness information from another communication terminal by BLE communication (step S615/Yes), the communication terminal 22 causes the presentation device 11 of the user to emit light having a color, brightness, and/or pattern corresponding to the kindness ranking of the user acquired in the above step S603 (step S618).

Subsequently, after a fixed amount of time elapses, the communication terminal 22 controls the turning off of light from the presentation device 11 (step S921).

With this arrangement, when persons who have performed acts of kindness are present near each other and their respective communication terminals 22 communicate, by having the presentation devices 11 light up in a specific pattern, color, or the like, kind persons can recognize each other unobtrusively. By encouraging exchange between persons performing acts of kindness, without declaring that oneself has performed acts of kindness in a one-sided manner to many others with a communication tool such as a social networking service (SNS), communication is revitalized, and a feeling of wanting to be kinder in daily life is implanted.

In addition, an application in a shop whose objective is to facilitate exchange between persons performing acts of kindness is also conceivable. In such a shop, the light, color, and music (BGM) inside the shop may be adjusted in accordance with the kindness count of each user to create a tranquil, warm space, for example. Also, by making the lighting and music darker when a person with a kindness count of 0 enters such a shop, it is possible to make a shop where persons who are not kind are less likely to enter and where more kind and good persons congregate naturally, thereby developing a desire of wanting to be kind in order to enter a shop with a good atmosphere.

Additionally, in the operating process described with reference to FIG. 18, kindness information is transmitted and received between communication terminals 22, but the present applied example is not limited thereto. For example, in the case of recognizing that a person who has performed acts of kindness is nearby on the basis of the current actions (specifically, position information) of users accumulated periodically in an action management server, the matching server 31 may control the reception of kindness information with the communication terminal of a target person by BLE communication.

3-3. Third Applied Example

In addition, as a third applied example, it is also possible to provide action guidance so that a person wanting to perform an act of kindness and a person wanting to receive an act of kindness move closer to each other. For example, when a pregnant woman is waiting for a train on a platform, if the pregnant woman could know in advance which car a person who would give up his or her seat is riding in, the pregnant woman could board the specified car and thereby enable an unobtrusive act of kindness to occur more easily. Also, if a person wanting to perform an act of kindness could know the position of a person wanting to receive an act of kindness, the person could move to that position to enable an unobtrusive act of kindness to occur more easily.

Specifically, instead of just transmitting a help signal by BLE communication from the communication terminal of a person wanting to receive an act of kindness to a surrounding communication terminal, for example, email or the like may be used to transmit a help mail message including the current state and current position (such as "boarding car N of the E train" or "waiting for the E train at F station", for example) to persons able to help (that is, persons wanting to perform an act of kindness) who exist over a wide range.

Also, from the communication terminal of a person wanting to perform an act of kindness, a handling mail message including the current state and current position (such as "boarding car M of the E train" or "riding in car M of the E train due to arrive next at F station", for example) may be transmitted in reply to the help mail message. With this arrangement, a person wanting to perform an act of kindness can take action to perform an act of kindness, while in addition, a person wanting to receive an act of kindness can move to a place where an act of kindness could be received.

4. CONCLUSION

As described above, with an act-of-kindness support system according to an embodiment of the present disclosure, by acquiring the situation of a user and notifying surroundings, it becomes possible to encourage unobtrusive acts of kindness.

Also, by progressively issuing unobtrusive notifications such as with vibration, display, and light on the side that performs the act of kindness and the side that receives the act of kindness, the person performing the act of kindness and the person receiving the act of kindness can recognize each other without being noticed by other people around.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it is possible to create a computer program for causing hardware such as a CPU, ROM, and RAM built into the presentation device 11, the communication terminal 22, or the matching server 31 described above to exhibit the functions of the presentation device 11, the communication terminal 22, or the matching server 31. A computer-readable storage medium made to store such a computer program is also provided.

In addition, the communication terminal 21 or 22 and the presentation device 11 according to the present embodiment may also be integrated.

Further, the effects described in this specification are merely illustrative or exemplified effects, and are not limitative. That is, with or in the place of the above effects, the technology according to the present disclosure may achieve other effects that are clear to those skilled in the art from the description of this specification. Additionally, the present technology may also be configured as below.

(1)

A communication device including:

a control unit that acquires current situation information of a first user based on an attribute of the first user and a current situation of the first user; and a communication unit that, in accordance with control by the control unit, transmits the current situation information of the first user to a surrounding communication device.

(2)

The communication device according to (1), in which the control unit acquires the current situation information of the first user by generating current situation information in accordance with the attribute of the first user and the current situation of the first user, and the communication unit transmits the generated current situation information to one or more surrounding communication devices.

(3)

The communication device according to (2), in which the communication unit receives a signal from one of the surrounding communication devices, the signal indicating that a situation indicated by the current situation information is handleable, and the communication device further includes a notification unit that, in accordance with control by the control unit, notifies the first user that the signal indicating that the situation is handleable has been received.

(4)

The communication device according to (3), in which the communication unit receives a signal requesting a presence notification to surroundings from one of the surrounding communication devices, and the notification unit, in accordance with control by the control unit, notifies the first user that the signal requesting a presence notification to surroundings has been received.

(5)

The communication device according to (4), further including:

an input unit that accepts an input of approval by the first user with respect to the signal requesting a presence notification to surroundings, in which if the input of approval is performed, the control unit controls a notification by the notification unit of own presence to surroundings.

(6)

The communication device according to (5), in which the notification unit issues a presence notification to surroundings by light emission.

(7)

The communication device according to any one of (2) to (6), in which the current situation information of the first user indicates an action currently desired by the first user, the action being determined on a basis of a combination of the attribute of the first user and the current situation of the first user, and the signal indicating that the situation is handleable indicates that another unspecified user is able to help the first user.

(8)

The communication device according to (2), in which the communication unit receives attribute information of an object existing around the communication device from a device affixed to the object, and the control unit generates the current situation information in accordance with the attribute of the first user, and the attribute information of the object as the current situation of the first user.

(9)

The communication device according to (8), in which the current situation information is an advisability of providing the object to the first user, the advisability being determined on a basis of allergy information included in the attribute of the first user and allergen information included in the attribute information of the object as the current situation of the first user.

(10)

The communication device according to (1), in which the communication unit, in accordance with control by the control unit, transmits the current situation information of the first user based on the attribute of the first user and the current situation of the first user to one or more surrounding communication devices, and additionally transmits the current situation information in association with the first user to a server.

(11)

The communication device according to (10), in which the current situation of the first user is extracted by the control unit on a basis of sensing data of the first user, and the attribute of the first user is received from the server by the communication unit.

(12)

The communication device according to (10) or (11), in which the communication unit receives a signal indicating that one of the surrounding communication devices is capable of handling a situation indicated by the current situation information, and the communication device further includes a notification unit that, in accordance with control by the control unit, notifies the first user that the signal indicating that the situation is handleable has been received.

(13)

The communication device according to (12), in which the communication unit receives a signal requesting a presence notification to surroundings from one of the surrounding notification devices, and the notification unit, in accordance with control by the control unit, notifies the first user that the signal requesting a presence notification to surroundings has been received.

(14)

The communication device according to (13), further including:

an input unit that accepts an input of approval by the first user with respect to the signal requesting a presence notification to surroundings, in which if the input of approval is performed, the control unit controls a notification by the notification unit of own presence to surroundings.

(15)

The communication device according to (1), in which the communication unit receives attribute information of an object existing around the communication device from a device affixed to the object, the control unit generates attribute information of the object associated with the first user as the current situation of the first user, and the communication unit transmits the attribute information of the object generated as the current situation of the first user to a server, receives the current situation information of the first user generated by the server in accordance with the attribute of the first user and the attribute information of the object, and transmits the received current situation information to one or more surrounding communication devices.

(16)

The communication device according to (1), further including:

a light emission unit that, in accordance with control by the control unit, emits light on a basis of a situation handling history for other users by each possessing user of the surrounding communication device, and a situation handling history for other users by the first user.

(17)

The communication device according to (16), in which the communication unit, in accordance with control by the control unit, acquires the situation handling history for other users by the first user from a server, notifies the surrounding communication device in accordance with the acquired situation handling history, and receives from the surrounding communication device the situation handling history for other users by the possessing user of the surrounding communication device, and the light emission unit, in accordance with control by the control unit, emits light in accordance with the received history of the possessing user of the surrounding communication device and the history of the first user acquired from the server.

(18)

An information processing system including:

a storage unit that stores at least an attribute of a first user and an attribute of a second user;

a communication unit that receives, from a first communication device, a current situation associated with the first user and generated current situation information, and receives, from a second communication device, a signal associated with the second user and indicating that the second communication device has received the current situation information from the first communication device; and a control unit that, on a basis of the attribute of the first user, the current situation information, and the attribute of the second user, controls a transmission of a signal to the second communication device determined to be capable of handling a situation of the first user indicated by the current situation information, the signal indicating that a user seeking handling from surroundings exists.

(19)

The information processing system according to (18), in which in a case in which there are a plurality of communication devices capable of handling the situation of the first user, the control unit selects one communication device, and controls the transmission of the signal indicating that a user seeking handling from surroundings exists.

(20)

The information processing system according to (18) or (19), in which the control unit controls, via the communication unit, a transmission to the first communication device of a signal indicating that a surrounding communication device is capable of handling the current situation of the first user.

(21)

The information processing system according to any one of (18) to (20), in which the storage unit, in accordance with control by the control unit, records a handling of the current situation of the first user by the second user as a history.

(22)

The information processing system according to (21), in which the control unit recognizes that the second user has handled the current situation of the first user on a basis of a change in a current situation associated with the first user transmitted from the first communication device and a change in a current situation associated with the second user transmitted from the second communication device, and controls a storage of the handling as a history in the storage unit.

(23)

An information processing system including:

a storage unit that stores an attribute of a first user and attribute information of a specific object;

a communication unit that receives, from a first communication device, identification information of a specific object disposed around the first user and identification information of the first user as a current situation associated with the first user; and a control unit that, in a case of determining that the first user is a user who needs to seek handling from surroundings on a basis of a relationship between the attribute of the first user and the attribute information of the specific object, controls a transmission to the first communication device via the communication unit of an indication of a need to seek handling from surroundings.

(24)

A computer-readable recording medium on which a program is recorded, the program causing a computer to function as:

a control unit that acquires current situation information of a first user based on an attribute of the first user and a current situation of the first user; and a communication unit that, in accordance with control by the control unit, transmits the current situation information of the first user to a surrounding communication device.

(25)

An information processing method including:

receiving, by a communication unit, from a first communication device, a current situation associated with a first user and generated current situation information, and receiving, from a second communication device, a signal associated with a second user and indicating that the second communication device has received the current situation information from the first communication device; and controlling, by a control unit, on a basis of an attribute of the first user stored in a storage unit, the received current situation information, and an attribute of the second user stored in the storage unit, a transmission of a signal to the second communication device determined to be capable of handling a situation of the first user indicated by the current situation information, the signal indicating that a user seeking handling from surroundings exists.

(26)

An information processing method including: receiving, by a communication unit, from a first communication device, identification information of a specific object disposed around a first user and identification information of the first user as a current situation associated with the first user; and controlling, by a control unit, in a case of determining that the first user is a user who needs to seek handling from surroundings on a basis of a relationship between an attribute of the first user and attribute information of the specific object stored in a storage unit in association with the respective pieces of identification information, a transmission to the first communication device via the communication unit of an indication of a need to seek handling from surroundings.

REFERENCE SIGNS LIST

11 (11A, 11B) presentation device
111 control unit
112 short-range communication unit
113 position information acquisition unit
114 acceleration sensor
115 light emission unit
116 vibration unit
21 (21A, 21B), 22 (22A, 22B) communication terminal
211, 221 control unit
   2110, 2210 situation acquisition unit
   2111, 2211 situation information generation unit
   2112, 2212 communication control unit
   2113 handleability determination unit
   2114, 2213 presentation control unit 2115 act-of-kindness determination unit
2116 storage control unit
2121 network I/F
2122, 2222 short-range communication unit
213, 223 operation input unit
214, 224 microphone
215, 225 camera
216, 226 display unit
217, 227 speaker
218 attribute storage unit
219 act-of-kindness storage unit
31 matching server
311 control unit
3111 situation information acquisition unit
3112 communication control unit
3113 matching processing unit
3114 act-of-kindness determination unit
3115 storage control unit
313 act-of-kindness storage unit
41 attribute management server
50 network
101, 102 act-of-kindness support system
511, 512, 513 ID tag

The invention claimed is:

1. A communication device, comprising:
circuitry configured to:
acquire current situation information based on an attribute of a first user and a current situation of the first user;
transmit the current situation information to at least one surrounding communication device;
receive a first signal from a surrounding communication device of the at least one surrounding communication device, wherein the first signal includes a request for a presence notification to surroundings; and
notify own presence to the surroundings based on an approval for the request by the first user.

2. The communication device according to claim 1, wherein the circuitry is further configured to:
generate the current situation information based on the attribute and the current situation; and
transmit the generated current situation information to the at least one surrounding communication device.

3. The communication device according to claim 2, wherein the circuitry is further configured to:
receive a second signal from one of the at least one surrounding communication device, wherein the received second signal indicates a handleability of a situation associated with the current situation information; and
notify the first user of the reception of the second signal.

4. The communication device according to claim 3, wherein the circuitry is further configured to notify the first user of the reception of the first signal.

5. The communication device according to claim 1, wherein the circuitry is further configured to accept an input of the approval by the first user based on the received first signal.

6. The communication device according to claim 4, wherein the circuitry is further configured to issue the presence notification to the surroundings by light emission.

7. The communication device according to claim 2, wherein
the current situation information of the first user indicates an action currently desired by the first user, the action is based on the attribute and the current situation, and
a second signal indicates an ability of an unspecified user to help the first user.

8. The communication device according to claim 2, wherein the circuitry is further configured to:
receive attribute information from a device affixed to an object, wherein the attribute information corresponds to the object in a specific proximity to the communication device; and
generate the current situation information based on the attribute of the first user and the attribute information of the object, wherein the current situation information corresponds to the current situation of the first user.

9. The communication device according to claim 8, wherein
the current situation information is an advisability to the first user, and
the advisability indicates a provision of the object to the first user based on allergy information associated with the attribute and allergen information associated with the attribute information of the object.

10. The communication device according to claim 1, wherein the circuitry is further configured to transmit the current situation information of the first user to each of:
the at least one surrounding communication device; and
a server.

11. The communication device according to claim 10, wherein the circuitry is further configured to:
extract the current situation of the first user based on sensor data of the first user; and
receive the attribute of the first user from the server.

12. The communication device according to claim 10, wherein the circuitry is further configured to:
receive a second signal from the server, wherein the second signal indicates that a second user associated with one of the at least one surrounding communication device has capability to handle the current situation associated with the transmitted current situation information of the first user; and
notify the first user of the reception of the second signal.

13. The communication device according to claim 12, wherein the circuitry is further configured to notify the first user of the reception of the first signal.

14. The communication device according to claim 1, wherein the circuitry is further configured to:
receive attribute information from a device affixed to an object, wherein the attribute information corresponds to the object in a specific proximity to the communication device;
generate new attribute information of the object associated with the first user, wherein the new attribute information corresponds to the current situation;
transmit the new attribute information of the object to a server, wherein the server generates new current situation information based on the attribute of the first user and the new attribute information of the object;
receive the new current situation information of the first user from the server; and
transmit the received new current situation information to the at least one surrounding communication device.

15. A non-transitory computer-readable having stored thereon computer-executable instructions which, when executed by a computer, cause the computer to execute operations, the operations comprising:

acquiring current situation information based on an attribute of a first user and a current situation of the first user;

transmitting the current situation information to at least one surrounding communication device;

receiving a first signal from a surrounding communication device of the at least one surrounding communication device, wherein the first signal includes a request for a presence notification to surroundings; and notifying own presence to the surroundings based on an approval for the request by the first user.

16. An information processing method, comprising:

in a communication device:

acquiring current situation information based on an attribute of a first user and a current situation of the first user;

transmitting the current situation information to at least one surrounding communication device;

receiving a first signal from a surrounding communication device of the at least one surrounding communication device, wherein the first signal includes a request for a presence notification to surroundings; and notifying own presence to the surroundings based on an approval for the request by the first user.

* * * * *